United States Patent
Chambers et al.

(10) Patent No.: US 6,730,681 B2
(45) Date of Patent: May 4, 2004

(54) TRIAZOLO-PYRIMIDINE DERIVATIVES AS LIGANDS FOR GABA RECEPTORS

(75) Inventors: Mark Stuart Chambers, Puckeridge (GB); Ian James Collins, Ware (GB); Simon Charles Goodacre, Benington (GB); David James Hallett, Watford (GB); Philip Jones, Bishops Stortford (GB); Linda Elizabeth Keown, Great Dunmow (GB); Robert James Maxey, Amersham (GB); Leslie Joseph Street, Little Hallingbury (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 10/149,851

(22) PCT Filed: Dec. 5, 2000

(86) PCT No.: PCT/GB00/04654

§ 371 (c)(1),
(2), (4) Date: Jun. 14, 2002

(87) PCT Pub. No.: WO01/44249

PCT Pub. Date: Jun. 21, 2001

(65) Prior Publication Data

US 2003/0045532 A1 Mar. 6, 2003

(30) Foreign Application Priority Data

Dec. 15, 1999 (GB) .............................. 9929687

(51) Int. Cl.⁷ .................. A61K 31/519; C07D 471/12; C07D 487/04

(52) U.S. Cl. ................ 514/262.1; 514/257; 514/228.8; 514/224.2; 514/232.5; 514/254; 514/218; 540/492; 540/470; 540/553; 540/575; 544/81; 544/82; 544/60; 544/61; 544/115; 544/118; 544/238; 544/251; 544/256; 544/47

(58) Field of Search ................................ 544/256, 251, 544/81, 61, 238, 47; 514/257, 258, 262.1, 228.8, 224.2, 232.5; 540/492, 575

(56) References Cited

FOREIGN PATENT DOCUMENTS

| WO | WO 98/04559 | 2/1998 |
|---|---|---|
| WO | WO 99/37645 | 7/1999 |
| WO | WO 99/65907 | 12/1999 |

OTHER PUBLICATIONS

Chemical Abstracts, vol. 80, No. 25, Jun. 24, 1974 J. Chem. Soc., Perkin Trans, 1, vol. 4, 1974, p. 534–540.
Biagi G; "1,2,3–Triazolo(1,5–a)Quinazolines . . . " Farmaco, IT, Societa Chimica Italiana, vol. 51, No. 2 Feb. 1996.
Bertelli L et al.: "Substituted 1,2,3–triazolo[1,5–a]quinazolines . . . " vol. 35, No. 3 Mar. 2000 pp. 333–341, p. 337.

*Primary Examiner*—John M. Ford
(74) *Attorney, Agent, or Firm*—J. Eric Thies; Melvin Winokur

(57) ABSTRACT

A class of substituted or 6,7-ring fused [1, 2, 3]triazolo[1, 5-α]-pyrimidine derivatives, possessing an optionally substituted cycloalkyl, phenyl or heteroaryl substituent at the 3-position and an amino moiety at the 5-position, are selective ligands for GABA$_A$ receptors, in particular having high affinity for the α2 and/or α3 subunit thereof, and are accordingly of benefit in the treatment and/or prevention of disorders of the central nervous system, including anxiety and convulsions.

12 Claims, No Drawings

TRIAZOLO-PYRIMIDINE DERIVATIVES AS LIGANDS FOR GABA RECEPTORS

CROSS REFERENCE TO RELATED APPLICATIONS

This application is a U.S. National Phase application under 35 U.S.C. §371 of PCT Application No. PCT/GB00/04654, filed Dec. 5, 2000, which claims priority under 35 U.S.C. §119 from GB Application No. 9929587.3, filed Dec. 15, 1999.

The present invention relates to a class of substituted triazolo-pyrimidine derivatives and to their use in therapy. More particularly, this invention is concerned with substituted [1,2,3]triazolo[1,5-α]pyrimidine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six α subunits, four β subunits, three γ subunits, one δ subunit, one ε subunit and two ρ subunits.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, δ, ε and ρ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, α1β2γ2, α2β2/3γ2, α3βγ2/3, α2βγ1, α5β3γ2/3, α6βγ2, α6βδ and α4βδ. Subtype assemblies containing an α1 subunit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1β2, α2βγ2 or α3βγ2 subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which interact more favourably with the α2 and/or α3 subunit than with α1 will be effective in the treatment of anxiety with a reduced propensity to cause sedation. Also, agents which are antagonists or inverse agonists at α1 might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

WO 99/37645 describes a class of substituted and 7,8-ring fused [1,2,4]triazolo[4,3-b]pyridazine derivatives which are stated to be selective ligands for $GABA_A$ receptors beneficial in the treatment and/or prevention of neurological disorders including anxiety and convulsions. There is in that publication, however, no disclosure nor any suggestion that the central triazolo-pyridazine ring system can be replaced by any other ring system. In particular, there is no disclosure nor any suggestion in that publication that the specified triazolo-pyridazine ring system can be replaced by a [1,2,3]triazolo[1,5-α]pyrimidine ring system.

Co-pending International Patent Application No. PCT/GB99/01827, published on Dec. 23, 1999 as WO 99/65907, describes a class of substituted and 6,7-ring fused [1,2,3] triazolo[1,5-α]pyrimidine derivatives which are stated to be selective ligands for $GABA_A$ receptors beneficial in the treatment and/or prevention of neurological disorders including anxiety and convulsions. However, the compounds described therein all possess a substituted alkoxy moiety at the 5-position, none of the compounds described therein being substituted at the 5-position by a substituted amino moiety.

The present invention provides a class of triazolo-pyrimidine derivatives which possess desirable binding properties at various $GABA_A$ receptor subtypes The compounds in accordance with the present invention have good affinity as ligands for the α2 and/or α3 subunit of the human $GABA_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are $GABA_A$ receptor subtype ligands having a binding affinity ($K_i$) for the α2 and/or α3 subunit, as measured in the assay described hereinbelow, of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

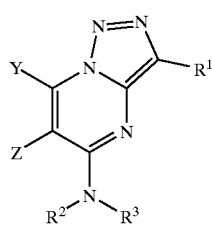

(I)

wherein
Y represents hydrogen or $C_{1-6}$ alkyl; and
Z represents $C_{1-6}$ alkyl, $C_{3-7}$ cycloalkyl, $C_{4-7}$ cycloalkenyl, $C_{6-8}$ bicycloalkyl, aryl, $C_{3-7}$ heterocycloalkyl, heteroaryl, $C_{2-7}$ alkoxycarbonyl or di($C_{1-6}$)alkylamino, any of which groups may be optionally substituted; or
Y and Z are taken together with the two intervening carbon atoms to form a ring selected from $C_{5-9}$ cycloalkenyl, $C_{6-10}$ bicycloalkenyl, tetrahydropyridinyl, pyridinyl and phenyl, any of which rings may be optionally benzo-fused and/or substituted;

$R^1$ represents $C_{3-7}$ cycloalkyl, phenyl, furyl, thienyl or pyridinyl, any of which groups may be optionally substituted;

$R^2$ represents hydrogen, $C_{1-6}$ alkyl, hydroxy($C_{1-6}$)alkyl or $C_{1-6}$ alkoxy($C_{1-6}$)alkyl; and $R^3$ represents $C_{1-6}$ alkyl, $C_{3-7}$ cycloalkyl($C_{1-6}$)alkyl, aryl($C_{1-6}$)alkyl, $C_{3-7}$ heterocycloalkyl or heteroaryl($C_{1-6}$) alkyl, any of which groups may be optionally substituted; or $R^2$ and $R^3$ are taken together with the intervening nitrogen atom to form a ring of formula (a), (b), (c), (d), (e), (f), (g), (h), (j) or (k):

(a)

(b)

(c)

(d)

(e)

(f)

(g)

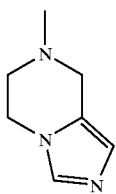

(h)

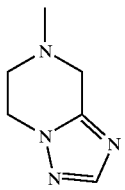

(j)

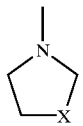

(k)

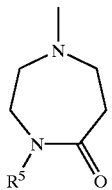

wherein

X represents oxygen, sulphur, N—$R^5$ or $CR^6R^7$;

$R^4$ represents hydrogen, $C_{1-6}$ alkyl, aryl, $C_{2-7}$ alkoxycarbonyl or aryl($C_{1-6}$)alkoxy($C_{1-6}$)alkyl;

$R^5$ represents hydrogen, $C_{1-6}$ alkyl, di($C_{1-6}$)alkylamino($C_{1-6}$)alkyl, $C_{2-6}$ alkenyl, $C_{3-7}$ cycloalkyl($C_{1-6}$)alkyl, aryl, $C_{3-7}$ heterocycloalkyl($C_{1-6}$)alkyl, heteroaryl, $C_{2-7}$ alkylcarbonyl or $C_{2-7}$ alkoxycarbonyl;

$R^6$ represents hydrogen, halogen, hydroxy, $C_{1-6}$ alkoxy, di($C_{1-6}$)alkylamino, $C_{2-7}$ alkoxycarbonyl, or an optionally substituted or phenyl ring-fused $C_{3-7}$ heterocycloalkyl group; and $R^7$ represents hydrogen, $C_{1-6}$ alkyl, or an optionally substituted aryl or aryl($C_{1-6}$)alkyl group.

The present invention also provides a compound of formula I as depicted above, or a salt or prodrug thereof, wherein Y, Z and $R^1$ are as defined above;

$R^2$ represents hydrogen, $C_{1-6}$ alkyl, hydroxy($C_{1-6}$)alkyl or $C_{1-6}$ alkoxy($C_{1-6}$)alkyl; and $R^3$ represents $C_{1-6}$ alkyl, $C_{3-7}$ cycloalkyl($C_{1-6}$)alkyl, aryl($C_{1-6}$)alkyl or heteroaryl($C_{1-6}$)alkyl, any of which groups may be optionally substituted; or $R^2$ and $R^3$ are taken together with the intervening nitrogen atom to form a ring of formula (a), (b), (c), (d), (e), (f), (g) or (h) as depicted above, wherein X, $R^4$ and $R^7$ are as defined above;

$R^5$ represents hydrogen, $C_{1-6}$ alkyl, $C_{2-6}$ alkenyl, aryl, heteroaryl, $C_{2-7}$ alkylcarbonyl or $C_{2-7}$ alkoxycarbonyl; and $R^6$ represents hydrogen, halogen, hydroxy, di($C_{1-6}$) alkylamino, $C_{3-7}$ heterocycloalkyl or $C_{2-7}$ alkoxycarbonyl.

Where Y and Z are taken together with the two intervening carbon atoms to form a ring, the resulting compounds of formula I above incorporate the relevant cycloalkenyl, bicycloalkenyl, tetrahydropyridinyl, pyridinyl or phenyl ring fused to the central triazolo-pyrimidine ring system as depicted in formula I.

Where Y and Z are taken together with the two intervening carbon atoms to form a $C_{5-9}$ cycloalkenyl ring, this ring may be a cyclopentenyl, cyclohexenyl, cycloheptenyl, cyclooctenyl or cyclononenyl ring, suitably cyclohexenyl or cycloheptenyl.

Where Y and Z are taken together with the two intervening carbon atoms to form a $C_{6-10}$ bicycloalkenyl ring, this ring may be a bicyclo[2.1.1]hex-2-enyl, bicyclo[2.2.1]hept-2-enyl, bicyclo[2.2.2]oct-2-enyl, bicyclo[3.2.2]non-6-enyl or bicyclo[3.3.2]dec-9-enyl ring, suitably bicyclo[2.2.1]hept-2-enyl, bicyclo[2.2.2]oct-2-enyl or bicyclo[3.2.2]non-6-enyl, and especially bicyclo[2.2.2]oct-2-enyl.

Where Y and Z are taken together with the two intervening carbon atoms to form a ring, this ring may be optionally benzo-fused. By way of illustration, Y and Z taken together with the two intervening carbon atoms may represent a benzo-fused cyclohexenyl ring, whereby the resulting ring is dihydronaphthyl.

The groups Y, Z, $R^1$, $R^3$, $R^6$ and $R^7$ may be unsubstituted, or substituted by one or more, suitably by one or two, substituents. In general, the groups Y, Z, $R^1$, $R^3$, $R^6$ and $R^7$ will be unsubstituted or monosubstituted. Examples of optional substituents on the groups Y, Z, $R^1$, $R^3$, $R^6$ and $R^7$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$ alkoxy, $C_{3-7}$ cycloalkyl($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl. Representative substituents include $C_{1-6}$ alkyl, aryl($C_{1-6}$) alkyl, halogen, cyano, hydroxy, hydroxymethyl, $C_{1-6}$ alkoxy and $C_{3-7}$ cycloalkyl($C_{1-6}$)alkoxy. Particular substituents include methyl, ethyl, fluoro, chloro, hydroxy and methoxy. Additional substituents include oxo; and $C_{2-7}$ alkoxycarbonyl, e.g. methoxycarbonyl or ethoxycarbonyl. Specific substituents include methyl, fluoro, hydroxy, methoxy, oxo and ethoxycarbonyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl and 1,1-dimethylpropyl. Derived expressions such as "$C_{1-6}$ alkoxy" are to be construed accordingly.

Typical $C_{2-6}$ alkenyl groups include vinyl and allyl.

Typical $C_{3-7}$ cycloalkyl groups include cyclopropyl, cyclobutyl, cyclopentyl and cyclohexyl.

The expression "$C_{3-7}$ cycloalkyl($C_{1-6}$)alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl, thiomorpholinyl and diazepanyl groups.

A typical phenyl ring-fused $C_{3-7}$ heterocycloalkyl group is 1,2,3,4-tetrahydroisoquinolinyl.

A typical $C_{3-7}$ heterocycloalkyl($C_{1-6}$)alkyl group is pyrrolidinylethyl.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitably, Y represents hydrogen or methyl, especially hydrogen.

Examples of suitable values for the substituent Z include methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, bicyclo[2.1.1]hex-1-yl, bicyclo[2.2.1]heptan-1-yl, phenyl, pyrrolidinyl, methyl-pyrrolidinyl, piperidinyl, morpholinyl, thiomorpholinyl, pyridinyl, furyl, thienyl, chloro-thienyl, methoxycarbonyl and diethylamino, especially tert-butyl, cyclobutyl or phenyl.

In a particular embodiment, the substituent Z represents $C_{3-7}$ cycloalkyl, either unsubstituted or substituted by $C_{1-6}$ alkyl, especially methyl. Favourably, Z represents cyclobutyl.

When Y and Z are taken together with the two intervening carbon atoms to form a ring, representative compounds according to the invention include those of structure IA to IL:

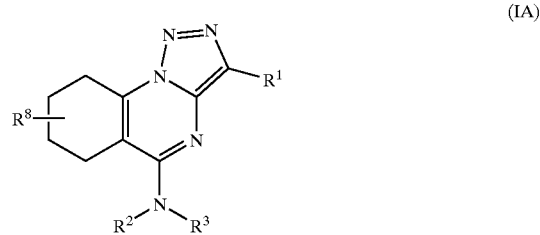
(IA)

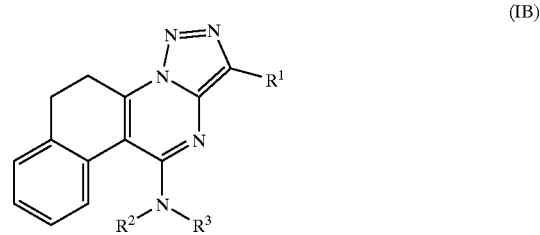
(IB)

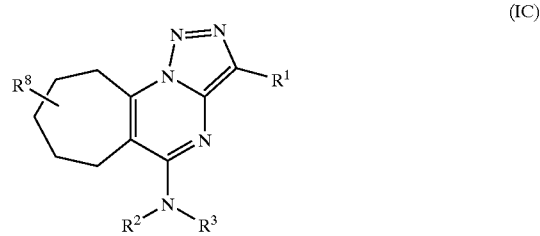
(IC)

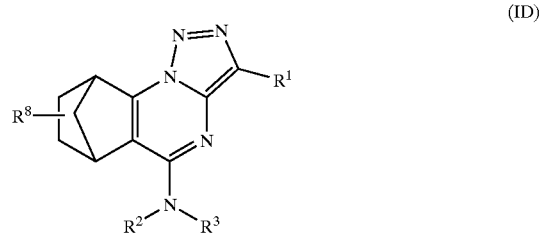
(ID)

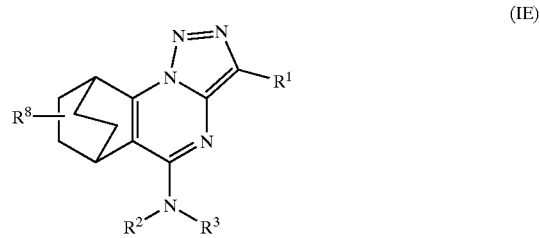
(IE)

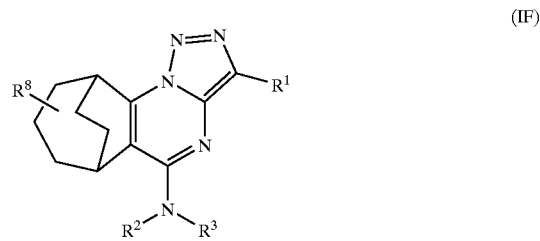
(IF)

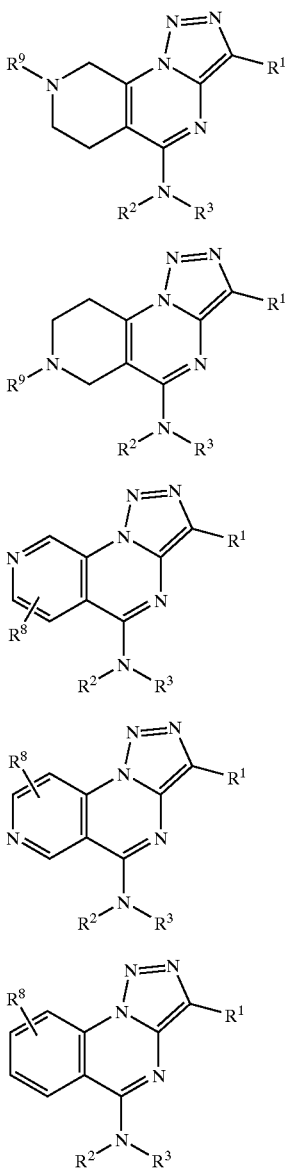

wherein $R^1$, $R^2$ and $R^3$ are as defined above;

$R^8$ represents hydrogen, $C_{1-6}$ alkyl, aryl($C_{1-6}$)alkyl, halogen, cyano, hydroxy, hydroxymethyl or $C_{1-6}$ alkoxy; and $R^9$ represents hydrogen or $C_{1-6}$ alkyl.

Suitably, $R^8$ represents hydrogen, $C_{1-6}$ alkyl or halogen, especially hydrogen, methyl, fluoro or chloro. Particular values of $R^8$ include hydrogen and fluoro, especially hydrogen.

Suitably, $R^9$ represents hydrogen or methyl

Favoured ring-fused triazolo-pyrimidine derivatives according to the present invention include the compounds represented by formula IL as depicted above.

Examples of typical optional substituents on the group $R^1$ include methyl, fluoro and methoxy, especially fluoro.

Representative values of $R^1$ include cyclopropyl, phenyl, methylphenyl, fluorophenyl, difluorophenyl, trifluorophenyl, methoxyphenyl, furyl, thienyl, methyl-thienyl and pyridinyl. More particularly, $R^1$ may represent unsubstituted or monosubstituted phenyl. Most particularly, $R^1$ represents phenyl or fluorophenyl, especially fluorophenyl. A specific value of $R^1$ is 2-fluorophenyl.

Suitably, $R^2$ represents hydrogen, methyl, hydroxyethyl or methoxyethyl. Specific values of $R^2$ include 2-hydroxyethyl and 2-methoxyethyl.

Suitably, $R^3$ represents aryl($C_{1-6}$)alkyl or heteroaryl ($C_{1-6}$)alkyl, either of which groups may be optionally substituted.

Suitable values for the substituent $R^3$ in the compounds according to the invention include cyclohexylmethyl, benzyl, pyrazolylmethyl, isoxazolylmethyl, thiazolylmethyl, thiazolylethyl, imidazolylmethyl, benzimidazolylmethyl, oxadiazolylmethyl, triazolylmethyl, tetrazolylmethyl, pyridinylmethyl, pyridazinylmethyl, pyrimidinylmethyl, pyrazinylmethyl, quinolinylmethyl, isoquinolinylmethyl and quinoxalinylmethyl, any of which groups may be optionally substituted by one or more substituents.

Suitably, $R^3$ represents an optionally substituted triazolyl-methyl group.

Examples of suitable optional substituents on the group $R^3$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxymethyl, $C_{1-6}$ alkoxy, $C_{3-7}$ cycloalkyl($C_{1-6}$)alkoxy, amino($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl ($C_{1-6}$)alkyl and di($C_{1-6}$)alkylmorpholinyl($C_{1-6}$)alkyl, especially $C_{1-6}$ alkyl.

Specific illustrations of particular substituents on the group $R^3$ include methyl, ethyl, in-propyl, benzyl, pyridinylmethyl, chloro, chloromethyl, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl, morpholinylmethyl and dimethylmorpholinylmethyl, especially methyl or ethyl, and more especially methyl.

Representative values of $R^3$ include hydroxymethyl-cyclohexylmethyl, cyanobenzyl, hydroxymethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl, methyl-imidazolylmethyl, ethyl-imidazolylmethyl, benzyl-imidazolylmethyl, benzimidazolylmethyl, methyl-oxadiazolylmethyl, triazolylmethyl, methyl-triazolylmethyl, ethyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, aminoethyl-triazolylmethyl, dimethylaminoethyl-triazolylmethyl, dimethylaminocarbonylmethyl-triazolylmethyl, N-methylpiperidinyl-triazolylmethyl, pyrrolidinylethyl-triazolylmethyl, piperazinylethyl-triazolylmethyl, morpholinylethyl-triazolylmethyl, methyl-tetrazolylmethyl, pyridinylmethyl, methyl-pyridinylmethyl, dimethyl-pyridinylmethyl, ethoxy-pyridinylmethyl, cyclopropylmethoxy-pyridinylmethyl, pyridazinylmethyl, chloro-pyridazinylmethyl, pyrimidinylmethyl, pyrazinylmethyl, quinolinylmethyl, isoquinolinylmethyl and quinoxalinylmethyl Particular values of $R^3$ include methyl-triazolylmethyl and ethyl-triazolylmethyl.

A favoured value of $R^3$ is methyl-triazolylmethyl.

In an alternative embodiment, $R^3$ suitably represents a substituted $C_{1-6}$ alkyl group. In a particular aspect of this embodiment, $R^3$ represents ethyl substituted by hydroxy or methoxy. Specific values of $R^3$ in this context include 2-hydroxyethyl and 2-methoxyethyl.

In a further embodiment, $R^3$ suitably represents an optionally substituted $C_{3-7}$ heterocycloalkyl group. In a particular aspect of this embodiment, $R^3$ represents piperidinyl, either unsubstituted or substituted by $C_{1-6}$ alkyl, e.g. methyl. A specific value of $R^3$ in this context is 1-methylpiperidin-4-yl.

Where $R^2$ and $R^3$ are taken together with the intervening nitrogen atom to form a ring, this is suitably a ring of formula (a), (b), (d), (f), (g) or (h) as depicted above.

Suitably, $R^4$ may represent hydrogen or $C_{2-7}$ alkoxycarbonyl. Particular values of $R^4$ include hydrogen and ethoxycarbonyl, especially hydrogen.

Suitably, $R^5$ may represent hydrogen, $C_{1-6}$ alkyl, aryl or heteroaryl. Typical values of $R^5$ include hydrogen, methyl, ethyl, n-propyl, dimethylaminoethyl, allyl, cyclopropylmethyl, phenyl, pyrrolidinylethyl, pyridinyl, acetyl, propionyl, trimethylacetyl and ethoxycarbonyl. Specific values of $R^5$ include hydrogen, methyl, ethyl, n-propyl, allyl, phenyl, pyridinyl, acetyl, propionyl, trimethylacetyl and ethoxycarbonyl. Particular values of $R^5$ include hydrogen, methyl, phenyl and pyridinyl.

Suitably, $R^6$ may represent hydrogen, hydroxy, di($C_{1-6}$)alkylamino, $C_{3-7}$ heterocycloalkyl or $C_{2-7}$ alkoxycarbonyl. Typical values of $R^6$ include hydrogen, hydroxy, methoxy, dimethylamino, pyrrolidinyl, piperidinyl, ethoxycarbonyl-piperidinyl, morpholinyl, diazepanonyl, 1,2,3,4-tetrahydroisoquinolinyl and ethoxycarbonyl. Particular values of $R^6$ include hydrogen, hydroxy, dimethylamino, pyrrolidinyl, piperidinyl and ethoxycarbonyl.

An example of a typical optional substituent on the group $R^7$ is halogen, suitably chloro. Particular values of $R^7$ include hydrogen and $C_{1-6}$ alkyl, especially hydrogen or methyl.

A particular sub-class of compounds according to the invention is represented by the compounds of formula IIA, and salts and prodrugs thereof:

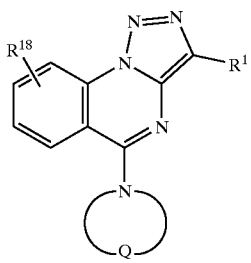

(IIA)

wherein
$R^1$ is as defined above;
$R^{18}$ represents hydrogen or halogen; and
Q represents the residue of a ring of formula (a), (b), (c), (d), (e), (f), (g), (h), (j) or (k) as defined with reference to formula I above.

The present invention also provides a compound of formula IIA as depicted above, or a salt or prodrug thereof, wherein
$R^1$ and $R^{18}$ are as defined above; and
Q represents the residue of a ring of formula (a) to (h) as defined with reference to formula I above.

Particular values of $R^{18}$ include hydrogen and fluoro, especially hydrogen.

Particular rings of which Q is the residue include the rings of formula (a), (b), (d), (f), (g) and (h) as depicted above.

A further sub-class of compounds according to the invention is represented by the compounds of formula IIB, and salts and prodrugs thereof:

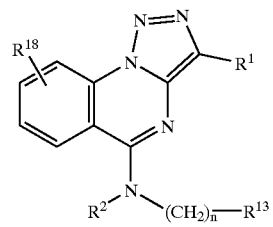

(IIB)

wherein
$R^1$ and $R^2$ are as defined with reference to formula I above;
$R^{18}$ is as defined with reference to formula IIA above;
n is 1 or 2; and
$R^{13}$ represents hydroxy or $C_{1-6}$ alkoxy, or an optionally substituted aryl or heteroaryl group.

In one embodiment of the compounds of formula IIB above, n is 2, and $R^{13}$ represents hydroxy or $C_{1-6}$ alkoxy. In a particular aspect of this embodiment, n is 2, and $R^{13}$ represents hydroxy or methoxy.

In another embodiment of the compounds of formula IIB, n is 1 or 2, typically 1, and $R^{13}$ represents an optionally substituted aryl or heteroaryl group.

Suitably, $R^{13}$ represents phenyl, pyrazolyl, isoxazolyl, thiazolyl, imidazolyl, benzimidazolyl, oxadiazolyl, triazolyl, tetrazolyl, pyridinyl, pyridazinyl, pyrimidinyl, pyrazinyl, quinolinyl, isoquinolinyl or quinoxalinyl, any of which groups may be optionally substituted.

A particular value of $R^{13}$ is optionally substituted triazolyl.

Examples of typical substituents on the group $R^{13}$ include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, amino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl and morpholinyl($C_{1-6}$)alkyl, especially $C_{1-6}$ alkyl Illustrative values of specific substituents on the group $R^{13}$ include methyl, ethyl, n-propyl, benzyl, pyridinylmethyl, chloro, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl and morpholinylmethyl, especially methyl or ethyl, and more especially methyl.

Representative values of $R^{13}$ include cyanophenyl, hydroxymethyl-phenyl, pyrazolyl, dimethyl-pyrazolyl, methyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-oxadiazolyl, triazolyl, methyl-triazolyl, ethyl-triazolyl, propyl-triazolyl, benzyl-triazolyl, pyridinylmethyl-triazolyl, cyanomethyl-triazolyl, dimethylaminomethyl-triazolyl, aminoethyl-triazolyl, dimethylaminoethyl-triazolyl, dimethylaminocarbonylmethyl-triazolyl, N-methylpiperidinyl-triazolyl, pyrrolidinylethyl-triazolyl, piperazinylethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyridazinyl, pyrimidinyl, pyrazinyl, quinolinyl, isoquinolinyl and quinoxalinyl.

Particular values of $R^{13}$ include methyl-triazolyl and ethyl-triazolyl.

A favoured value of $R^{13}$ is methyl-triazolyl.

A particular subset of the compounds of formula IIB above is represented by the compounds of formula IIC, and pharmaceutically acceptable salts thereof:

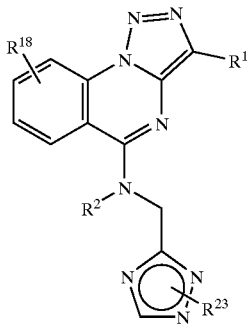

(IIC)

wherein $R^1$ and $R^2$ are as defined with reference to formula I above;

$R^{18}$ is as defined with reference to formula IIA above; and $R^{23}$ represents hydrogen, methyl or ethyl.

Suitably, $R^{23}$ represents methyl or ethyl, especially methyl.

Another sub-class of compounds according to the invention is represented by the compounds of formula IID, and salts and prodrugs thereof:

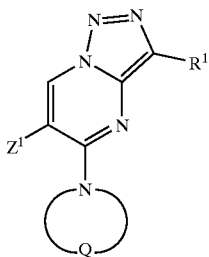

(IID)

wherein $R^1$ and Q are as defined above; and $Z^1$ represents $C_{1-6}$ alkyl, $C_{3-7}$ cycloalkyl or aryl, any of which groups may be optionally substituted.

Examples of typical substituents on the group $Z^1$ include $C_{1-6}$ alkyl, especially methyl.

Illustrative values for the group $Z^1$ include methyl, ethyl, isopropyl, tert-butyl, 1,1-dimethylpropyl, cyclopropyl, methyl-cyclopropyl, cyclobutyl, methyl-cyclobutyl, cyclopentyl, methyl-cyclopentyl, cyclohexyl and phenyl.

Particular values of $Z^1$ include tert-butyl, cyclobutyl and phenyl.

In a specific embodiment, $Z^1$ represents cyclobutyl. In another embodiment, $Z^1$ represents phenyl.

An additional sub-class of compounds according to the invention is represented by the compounds of formula IIE, and salts and prodrugs thereof:

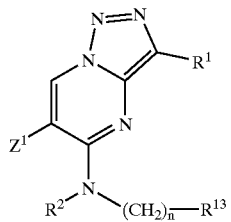

(IIE)

wherein $R^1$, $R^2$, n, $R^{13}$ and $Z^1$ are as defined above.

A particular subset of the compounds of formula IIE above is represented by the compounds of formula IIF, and salts and prodrugs thereof:

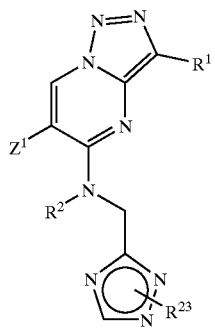

(IIF)

wherein $R^1$ and $R^2$ are as defined with reference to formula I above;

$R^{23}$ is as defined with reference to formula IIC above; and $Z^1$ is as defined with reference to formula IID above.

Specific compounds within the scope of the present invention include:

3-(2-fluorophenyl)-5-(morpholin-4-yl)-[1,2,3]triazolo[1,5-α]quinazoline;

5-[5,6-dihydroimidazo[1,2-α]pyrazin-7(8H)-yl]-3-(2-fluorophenyl)-[1,2,3]triazolo[1,5-α]quinazoline;

5-[5,6-dihydroimidazo[1,5-α]pyrazin-7(8H)-yl]-3-(2-fluorophenyl)-[1,2,3]triazolo[1,5-α]quinazoline;

5-[5,6-dihydro[1,2,4]triazolo[1,5-α]pyrazin-7(8H)-yl]-3-(2-fluorophenyl)-[1,2,3]triazolo[1,5-α]quinazoline;

3-(2-fluorophenyl)-5-(3-oxo-4-phenylpiperazin-1-yl)-[1,2,3]triazolo[1,5-α]quinazoline;

5-(4-ethoxycarbonylpiperazin-1-yl)-3-(2-fluorophenyl)-[1,2,3]triazolo[1,5-α]quinazoline;

5-(3-ethoxycarbonylpiperidin-1-yl)-3-(2-fluorophenyl)-[1,2,3]triazolo[1,5-α]quinazoline;

5-(4-ethoxycarbonylpiperidin-1-yl)-3-(2-fluorophenyl)-[1,2,3]triazolo[1,5-α]quinazoline;

3-(2-fluorophenyl)-5-(4-hydroxypiperidin-1-yl)-[1,2,3]triazolo[1,5-α]quinazoline;

3-(2-fluorophenyl)-5-[4-(pyridin-4-yl)piperazin-1-yl]-[1,2,3]triazolo[1,5-α]quinazoline;

3-(2-fluorophenyl)-5-[4-(pyridin-2-yl)piperazin-1-yl]-[1,2,3]triazolo[1,5-α]quinazoline;

5-(4-acetylpiperazin-1-yl)-3-(2-fluorophenyl)-[1,2,3]triazolo[1,5-α]quinazoline;

3-(2-fluorophenyl)-5-[2-oxopiperazin-4(1H)-yl]-[1,2,3]triazolo[1,5-α]quinazoline;

3-(2-fluorophenyl)-5-(1-methyl-2-oxopiperazin-4-yl)-[1,2,3]triazolo[1,5-α]quinazoline;

5-[5,6-dihydroimidazo[1,2-α]pyrazin-7(8H)-yl]-7-fluoro-3-(2-fluorophenyl)-[1,2,3]triazolo[1,5-α]quinazoline;

5-[bis(2-methoxyethyl)amino]-3-(2-fluorophenyl)-[1,2,3]triazolo[1,5-α]quinazoline;

3-(2-fluorophenyl)-5-(thiomorpholin-4-yl)-[1,2,3]triazolo[1,5-α]quinazoline;

5-[4-(dimethylamino)piperidin-1-yl]-3-(2-fluorophenyl)-[1,2,3]triazolo[1,5-α]quinazoline;

3-(2-fluorophenyl)-5-[4-(pyrrolidin-1-yl)piperidin-1-yl]-[1,2,3]triazolo[1,5-α]quinazoline;

3-(2-fluorophenyl)-5-[4-(piperidin-1-yl)piperidin-1-yl]-[1,2,3]triazolo[1,5-α]quinazoline;

5-[bis(2-hydroxyethyl)amino]-3-(2-fluorophenyl)-[1,2,3]triazolo[1,5-α]quinazoline;

3-(2-fluorophenyl)-5-(4-oxopiperidin-1-yl)-[1,2,3]triazolo[1,5-α]quinazoline;

5-(1-ethyl-2-oxopiperazin-4-yl)-3-(2-fluorophenyl)-[1,2,3]triazolo[1,5-α]quinazoline;

3-(2-fluorophenyl)-5-(2-oxo-1-propylpiperazin-4-yl)-[1,2,3]triazolo[1,5-α]quinazoline;

3-(2-fluorophenyl)-5-[2-oxo-1-(2-propenyl)piperazin-4-yl]-[1,2,3]triazolo-[1,5-α]quinazoline;

3-(2-fluorophenyl)-5-(4-hydroxy-4-methylpiperidin-1-yl)-[1,2,3]triazolo-[1,5-α]quinazoline;

1-{4-[3-(2-fluorophenyl)-[1,2,3]triazolo[1,5-α]quinazolin-5-yl]piperazin-1-yl}propan-1-one;

2,2-dimethyl-1-{4-[3-(2-fluorophenyl)-[1,2,3]triazolo[1,5-α]quinazolin-5-yl]piperazin-1-yl}propan-1-one;

N-[3-(2-fluorophenyl)-[1,2,3]triazolo[1,5-α]quinazolin-5-yl]-N-methyl-N-(1-methylpiperidin-4-yl)amine;

1-[3-(2-fluorophenyl)-[1,2,3]triazolo[1,5-α]quinazolin-5-yl]-[1,4]diazepan-5one;

3-(2-fluorophenyl)-5-(piperidin-1-yl)-[1,2,3]triazolo[1,5-α]quinazoline;

3-(2-fluorophenyl)-5-[4-(morpholin-4-yl)piperidin-1-yl]-[1,2,3]triazolo[1,5-α]quinazoline;

4-(2-dimethylaminoethyl)-1-[3-(2-Fluorophenyl)-[1,2,3]triazolo[1,5-α]quinazolin-5-yl]-[1,4]diazepan-5-one;

1'-[3-(2-fluorophenyl)-[1,2,3]triazolo[1,5-α]quinazolin-5-yl]-[1,4']bipiperidinyl-4-carboxylic acid ethyl ester;

5-[4-(3,4-dihydro-1H-isoquinolin-2-yl)piperidin-1-yl]-3-(2-fluorophenyl)-[1,2,3]triazolo [1,5-α]quinazoline;

1-{1-[3-(2-fluorophenyl)-[1,2,3]triazolo[1,5-α]quinazolin-5-yl]piperidin-4-yl}[1,4]diazepan-5-one;

N,N-dimethyl-N-{1-[3-(2-fluorophenyl)-[1,2,3]triazolo[1,5-α]quinazolin-5-yl]pyrrolidin-3-yl}amine;

3-(2-fluorophenyl)-5-{4-[2-(pyrrolidin-1-yl)ethyl]piperazin-1-yl}-[1,2,3]triazolo[1,5-α]quinazoline;

3-(2-fluorophenyl)-5-(4-methoxypiperidin-1-yl)-[1,2,3]triazolo[1,5-α]quinazoline;

1-cyclopropylmethyl-4-[3-(2-fluorophenyl)-[1,2,3]triazolo[1,5-α]quinazolin-5-yl]piperazin-2-one;

and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the compounds of the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I as defined above may be prepared by a process which comprises reacting a compound of formula III with a compound of formula IV:

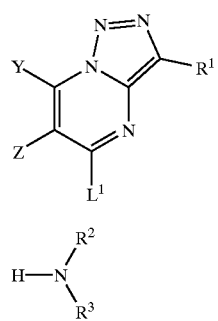

(III)

(IV)

wherein Y, Z, $R^1$, $R^2$ and $R^3$ are as defined above, and $L^1$ represents a suitable leaving group.

The leaving group $L^1$ is suitably an arylsulphonyloxy group such as p-toluenesulphonyloxy (tosyloxy).

The reaction between compounds III and IV is conveniently effected by stirring the reactants at an elevated temperature under basic conditions, for example triethylamine in N,N-dimethylformamide at a temperature in the region of 50° C.

The intermediates of formula III above wherein $L^1$ represents tosyloxy may be prepared by reacting a compound of formula V:

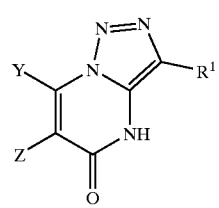

(V)

wherein Y, Z and $R^1$ are as defined above; with a tosylating agent, e.g. a tosyl halide such as tosyl chloride.

The reaction is conveniently carried out by stirring at ambient temperature in the presence of a base such as triethylamine, typically in a solvent such as N,N-dimethylformamide.

The intermediates of formula V above, in particular those wherein Y and Z are taken together with the two intervening carbon atoms to form a ring (e.g. a phenyl ring), may be prepared by reacting an azide derivative of formula VI with an acetonitrile derivative of formula VII:

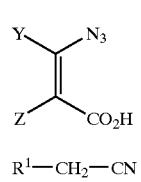

(VI)

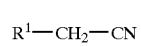

(VII)

wherein Y, Z and $R^1$ are as defined above.

The reaction between compounds VI and VII is conveniently effected under basic conditions in a suitable solvent, for example sodium ethoxide in ethanol, typically at an elevated temperature.

The intermediates of formula VI may be prepared by diazotisation of a compound of formula VIII:

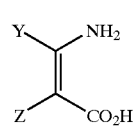

(VIII)

wherein Y and Z are as defined above; followed by displacement with azide ion.

The diazotisation/displacement procedure is conveniently effected by treating compound VIII with sodium nitrite at 0° C. in the presence of a mineral acid, e.g. hydrochloric acid, then with sodium azide, typically in the presence of sodium acetate.

In an alternative approach, the intermediates of formula V above, in particular those wherein Y and Z represent pendant groups (i.e. are not taken together with the intervening carbon atoms to form a ring), may be prepared by cyclising a compound of formula IX:

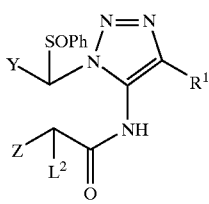

wherein Y, Z and $R^1$ are as defined above, $L^2$ represents a suitable leaving group, and Ph is an abbreviation for phenyl.

The leaving group $L^2$ is typically a halogen atom, especially chloro.

The cyclisation of compound IX is conveniently effected by treatment with a strong base, e.g. potassium bis(trimethylsilyl)amide, in the presence of a suitable solvent, e.g. tetrahydrofuran, typically at a temperature in the region of −78° C.

The intermediates of formula IX may be prepared by reacting a compound of formula X with a compound of formula XI:

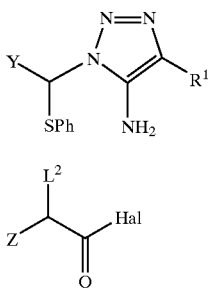

wherein Y, Z, $R^1$ and $L^2$ are as defined above, and Hal represents a halogen atom; followed by oxidation of the phenylthio group.

The halogen atom Hal in the compounds of formula XI is typically chloro.

The reaction between compounds X and XI is conveniently carried out in a solvent such as N,N-dimethylformamide, typically in the presence of pyridine, and suitably at a temperature in the region of 0° C. Subsequent oxidation of the phenylthio group is conveniently accomplished by treatment with ozone, typically in dichloromethane at a temperature in the region of −78° C.

The intermediates of formula X above may be prepared by reacting a compound of formula VII as defined above with a compound of formula XII:

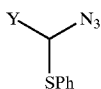

wherein Y is as defined above.

The reaction between compounds VII and XII is conveniently carried out by stirring the reactions in a suitable solvent, e.g. dimethylsulphoxide, typically in the presence of a base such as potassium carbonate.

Where they are not commercially available, the starting materials of formula IV, VII, VIII, XI and XII may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained wherein $R^3$ is unsubstituted may be converted into a corresponding compound wherein $R^3$ is substituted, typically by standard alkylation procedures, for example by treatment with a haloalkyl derivative in the presence of sodium hydride and N,N-dimethylformamide, or with a hydroxyalkyl derivative in the presence of triphenylphosphine and diethyl azodicarboxylate. Furthermore, a compound of formula I initially obtained wherein the $R^3$ substituent is substituted by a halogen atom, e.g. chloro, may be converted into the corresponding compound wherein the $R^3$ substituent is substituted by a di($C_{1-6}$)alkylamino moiety by treatment with the appropriate di($C_{1-6}$)alkylamine, typically with heating in a solvent such as 1,4-dioxane in a sealed tube. A compound of formula I wherein $R^5$ is hydrogen initially obtained may be converted into the corresponding compound of formula I wherein $R^5$ represents $C_{1-6}$ alkyl, $C_{3-6}$ alkenyl or $C_{3-7}$ heterocycloalkyl($C_{1-6}$)alkyl, typically by standard alkylation procedures, e.g. by treatment with the appropriate alkyl or alkenyl halide in the presence of a base such as sodium hydride or triethylamine and a solvent such as N,N-dimethylformamide. Moreover, a compound of formula I wherein $R^5$ is hydrogen initially obtained may be converted into the corresponding compound of formula I wherein $R^5$ represents $C_{2-7}$ alkoxycarbonyl by conventional acylation procedures, e.g. by treatment with the appropriate acyl halide. A compound of formula I wherein $R^6$ is hydroxy initially obtained may be converted into the corresponding compound of formula I wherein $R^6$ represents $C_{1-6}$ alkoxy by standard alkylation methods, e.g. by treatment with the appropriate alkyl halide, e.g. methyl iodide, in the presence of sodium hydride and N,N-dimethylacetamide. A compound of formula I initially obtained wherein —$NR^2R^3$ represents a ring of formula (d) may be converted by reductive amination into a compound of formula I wherein —$NR^2R^3$ represents a ring of formula (a) in which X is $CR^6R^7$, wherein $R^7$ is hydrogen and $R^6$ represents an N-linked heterocycloalkyl moiety, by treatment with the appropriate heterocycloalkane reagent, e.g. morpholine, in the presence of a reducing agent such as sodium triacetoxyborohydride.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic*

*Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 or α3 subunit stably expressed in Ltk$^-$ cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 subunit of the human $GABA_A$ receptor of 100 nM or less.

EXAMPLE 1

3-(2-Fluorophenyl)-5-(morpholin-4-yl)-[1,2,3]triazolo[1,5-α]quinazoline (a) 3-(2-Fluorophenyl)-[1,2,3]triazolo[1,5-α]quinazolin-5(4H)-one Sodium metal (1.4 g, 60 mmol) was dissolved in ethanol (100 ml) at room temperature under nitrogen. 2-Fluorophenylacetonitrile (3.85 ml, 30 mmol) was added, followed by the dropwise addition of a solution of 2-azidobenzoic acid (4.71 g, 29 mmol) in ethanol (60 ml). The thick white suspension was refluxed for 18 h then cooled and poured into water (800 ml). The mixture was acidified to pH 3–4 with aqueous 1M citric acid and the precipitated solid was collected. The solid was washed with diethyl ether (20 ml) and dried in vacuo to give 3-(2-fluorophenyl)-[1,2,3]triazolo[1,5-α]quinazolin-5(4H)-one (8.81 g, 100%), m.p. 238–241° C. (DMF). Found: C, 64.33; H, 3.06; N, 20.29. $C_{15}H_9FN_4O$ requires C, 64.28; H, 3.24; N, 19.99%. $δ_H$ (360 MHz; DMSO) 7.33–7.38 (2H, m), 7.46–7.55 (1H, m), 7.69–7.73 (2H, m), 8.02 (1H, ddd, J=9, 9 and 1), 8.24 (1H, dd, J=8 and 1), 8.38 (1H, d, J=8) and 12.40 (1H, br s); m/z (ES+) 821 (M+H$^+$).

(b) 3-(2-Fluorophenyl)-5-(4-methylbenzenesulfonyloxy)-[1,2,3]triazolo[1,5-α]quinazoline Triethylamine (5.6 ml, 40 mmol) was added to a stirred solution of 3-(2-fluorophenyl)-[1,2,3]triazolo[1,5-α]quinazolin-5(4H)-one (5.47 g, 19.5 mmol) and p-toluenesulfonyl chloride (3.82 g, 20 mmol) in dry N,N-dimethylformamide (100 ml) at room temperature under nitrogen. The brown suspension was stirred for 18 h then diluted with water (800 ml). The yellow precipitate was collected, washed sequentially with water and diethyl ether, then dried in vacuo to give 3-(2-fluorophenyl)-5-(4-methylbenzenesulfonyloxy)-[1,2,3]triazolo[1,5-α]quinazoline (8.65 g, 100%). $δ_H$ (400 MHz; CDCl$_3$) 2.42 (3H, s), 7.23 (2H, d, J=8), 7.28–7.34 (2H, m), 7.47–7.50 (1H, m), 7.76 (1H, dd, J=8 and 8), 7.87 (1H, ddd, J=7, 7 and 2), 8.04–8.08 (3H, m), 8.30 (1H, dd, J=8 and 1), 8.70 (1H, d, J=8); m/z (ES+) 435 (M+H$^+$).

(c) 3-(2-Fluorophenyl)-5-(morpholin-4-yl)-[1,2,3]triazolo[1,5-α]quinazoline

A solution of 3-(2-fluorophenyl)-5-(4-methylbenzenesulfonyloxy)-[1,2,3]triazolo[1,5-α]quinazoline (0.10 g, 0.23 mmol), triethylamine (0.10 ml, 0.7 mmol) and morpholine (0.025 g, 0.25 mmol) in dry N,N-dimethylformamide (2 ml) was stirred at 50° C. under nitrogen for 18 h. The mixture was cooled, then diluted with water (10 ml) and 10% methanol:dichloromethane (5 ml). The two phases were separated by filtration through a PTFE membrane and the organic layer was concentrated. Trituration and washing with ethyl acetate-diethyl ether gave 3-(2-fluorophenyl)-5-(morpholin-4-yl)-[1,2,3]triazolo[1,5-α]quinazoline (0.065 g, 81%). $δ_H$ (360 MHz; DMSO) 3.61 (4H, dd, J=5 and 5), 3.86 (4H, dd, J=5 and 5), 7.34–7.39 (2H, m), 7.42–7.50 (1H, m), 7.77 (1H, dd, J=7 and 7), 8.04–8.10 (2H, m), 8.22 (1H, d, J=8), 8.59 (1H, d, J=8); m/z (ES+) 350 (M+H$^+$).

EXAMPLE 2

5-[5,6-Dihydroimidazo[1,2-α]pyrazin-7(8H)-yl]-3-(2-fluorophenyl)-[1,2,3]triazolo[1,5-α]quinazoline Prepared from 5,6,7,8-tetrahydroimidazo[1,2-α]pyrazine as described for Example 1, step c (0.020 g, 23%). $δ_H$ (360 MHz; CDCl$_3$) 4.12 (2H, dd, J=6 and 6), 4.41 (2H, dd, J=6 and 6), 5.02 (2H, s), 6.93 (1H, s), 7.07 (1H, s), 7.21–7.32 (2H, m), 7.36–7.40 (1H, m), 7.68 (1H, dd, J=7 and 7), 7.95 (1H, dd, J=7 and 7), 8.07–8.10 (2H, m), 8.73 (1H, d, J=8); m/z (ES+) 386 (M+H$^+$).

EXAMPLE 3

5-[5,6-Dihydroimidazo[1,5-α]pyrazin-7(8H)-yl]-3-(2-fluorophenyl)-[1,2,3]triazolo[1,5-α]quinazoline Prepared from 5,6,7,8-tetrahydroimidazo[1,5-α]pyrazine as described for Example 1, step c (0.033 g, 37%). $δ_H$ (360

MHz; CDCl₃) 4.07 (2H, dd, J=6 and 6), 4.44 (2H, dd, J=6 and 6), 4.92 (2H, s), 6.93 (1H, s), 7.22–7.32 (2H, m), 7.37–7.41 (1H, m), 7.60 (1H, s), 7.69 (1H, dd, J=8 and 8), 7.96 (1H, dd, J=8 and 8), 8.05–8.09 (2H, m), 8.73 (1H, d, J=8); m/z (ES+) 386 (M+H⁺).

EXAMPLE 4

5-[5,6-Dihydro[1,2,4]triazolo[1,5-α]pyrazin-7(8H)-yl]-3-(2-fluorophenyl)-[1,2,3]triazolo[1,5-α]quinazoline Prepared from 5,6,7,8-tetrahydro[1,2,4]triazolo[1,5-α]pyrazine as described for Example 1, step c (0.047 g, 53%). Found: C, 62.52; H, 3.96; N, 29.10. $C_{20}H_{15}FN_8$ requires C, 62.17; H, 3.91; N, 29.00%. $\delta_H$ (360 MHz; CDCl₃) 4.16 (2H, dd, J=5 and 5), 4.61 (2H, dd, J=5 and 5), 5.02 (2H, s), 7.22–7.33 (2H, m), 7.40–7.42 (1H, m), 7.71 (1H, dd, J=8 and 8), 7.95–8.08 (4H, m), 8.75 (1H, d, J=8); m/z (ES+) 387 (M+H₊).

EXAMPLE 5

3-(2-Fluorophenyl)-5-(3-oxo-4-phenylpiperazin-1-yl)-[1,2,3]triazolo[1,5-α]quinazoline Prepared from 1-phenylpiperazin-2-one as described for Example 1, step c (0.054 g, 53%). $\delta_H$ (360 MHz; CDCl₃) 4.03–4.06 (2H, m), 4.10–4.13 (2H, m), 4.57 (2H, s), 7.20–7.46 (8H, m), 7.68 (1H, dd, J=8 and 8), 7.96 (1H, dd, J=8 and 8), 8.08–8.10 (2H, m), 8.73 (1H, d, J=8); m/z (ES+) 439 (M+H⁺).

EXAMPLE 6

5-(4-Ethoxycarbonylpiperazin-1-yl)-3-(2-fluorophenyl)-[1,2,3]triazolo[1,5-α]quinazoline Prepared from ethyl 1-piperazincarboxylate as described for Example 1, step c (0.034 g, 35%). $\delta_H$ (360 MHz; CDCl₃) 1.30 (3H, t, J=7), 3.61–3.64 (4H, m), 3.75–3.77 (4H, m), 4.19 (2H, q, J=7), 7.20–7.30 (2H, m), 7.34–7.40 (1H, m), 7.64 (1H, dd, J=8 and 8), 7.92 (1H, dd, J=8 and 8), 8.03 (1H, d, J=8), 8.11 (1H, ddd, J=8, 8 and 2), 8.72 (1H, d, J=8); m/z (ES+) 421 (M+H⁺).

EXAMPLE 7

5-(3-Ethoxycarbonylpiperidin-1-yl)-3-(2-fluorophenyl)-[1,2,3]triazolo[1,5-α]quinazoline Prepared from ethyl 3-piperidinecarboxylate as described for Example 1, step c (0.049 g, 49%). Found: C, 65.05; H, 5.22; N, 16.07. $C_{23}H_{22}FON_5 \cdot 0.33(H_2O)$ requires C, 64.94; H, 5.37; N, 16.46%. $\delta_H$ (360 MHz; DMSO) 1.14 (3H, t, J=7), 1.70–1.90 (3H, m), 2.00–2.10 (1H, m), 2.90–3.00 (1H, m), 3.35–3.50 (2H, m), 3.85–3.95 (1H, m), 4.05–4.11 (3H, m), 7.32–7.39 (2H, m), 7.40–7.45 (1H, m), 7.78 (1H, dd, J=8 and 8), 8.08 (1H, dd, J=8 and 8), 8.13 (1H, dd, J=8 and 8), 8.20 (1H, d, J=8), 8.58 (1H, d, J=8); m/z (ES+) 420 (M+H⁺).

EXAMPLE 8

5-(4-Ethoxycarbonylpiperidin-1-yl)-3-(2-fluorophenyl)-[1,2,3]triazolo[1,5-α]quinazoline Prepared from ethyl 4-piperidinecarboxylate as described for Example 1, step c (0.044 g, 44%). Found: C, 64.77; H, 5.15; N, 16.64. $C_{23}H_{22}FON_5 \cdot 0.33(H_2O)$ requires C, 64.94; H, 5.37; N, 16.46%. $\delta_H$ (360 MHz; DMSO) 1.21 (3H, t, J=7), 1.85–2.10 (4H, m), 2.65–2.75 (1H, m), 3.15–3.30 (2H, m), 4.00–4.15 (4H, m), 7.30–7.40 (2H, m), 7.42–7.50 (1H, m), 7.77 (1H, dd, J=8 and 8), 8.03–8.12 (2H, m), 8.17 (1H, d, J=8), 8.58 (1H, d, J=8); m/z (ES+) 420 (M+H⁺).

EXAMPLE 9

3-(2-Fluorophenyl)-5-(4-hydroxypiperidin-1-yl)-[1,2,3]triazolo[1,5-α]quinazoline Prepared from 4-hydroxypiperidine as described for Example 1, step c (0.050 g, 58%). $\delta_H$ (360 MHz; DMSO) 1.60–1.75 (2H, m), 1.90–2.05 (2H, m), 3.30–3.40 (2H, m), 3.79–3.82 (1H, m), 3.85–3.95 (2H, m), 4.80 (1H, d, J=4), 7.34–7.44 (3H, m), 7.77 (1H, dd, J=8 and 8), 8.05 (1H, dd, J=8 and 8), 8.12–8.16 (2H, m), 8.57 (1H, d, J=8); m/z (ES+) 364 (M+H⁺).

EXAMPLE 10

3-(2-Fluorophenyl)-5-[4-(pyridin-4-yl)piperazin-1-yl]-[1,2,3]triazolo[1,5-α]quinazoline Prepared from 1-(pyridin-4-yl)piperazine as described for Example 1, step c (0.067 g, 66%). $\delta_H$ (400 MHz; DMSO) 3.72–3.75 (4H, m), 3.80–3.83 (4H, m), 6.97–7.00 (2H, d, J=7), 7.35–7.40 (2H, m), 7.45–7.48 (1H, m), 7.80 (1H, dd, J=7 and 7), 8.09–8.11 (2H, m), 8.23 (2H, d, J=7), 8.28 (1H, d, J=7), 8.61 (1H, d, J=7); m/z (ES+) 426 (M+H⁺).

EXAMPLE 11

3-(2-Fluorophenyl)-5-[4-(pyridin-2-yl)piperazin-1-yl]-[1,2,3]triazolo[1,5-α]quinazoline Prepared from 1-(pyridin-2-yl)piperazine as described for Example 1, step c (0.069 g, 68%). $\delta_H$ (360 MHz; DMSO) 3.75–3.80 (8H, m), 6.69 (1H, dd, J=7 and 6), 6.90 (1H, d, J=7), 7.35–7.50 (3H, m), 7.58 (1H, dd, J=7 and 7), 7.80 (1H, dd, J=8 and 8), 8.08–8.16 (3H, m), 8.29 (1H, d, J=8), 8.60 (1H, d, J=7); m/z (ES+) 426 (M+H₊).

EXAMPLE 12

5-(4-Acetylpiperazin-1-yl)-3-(2-fluorophenyl)-[1,2,3]triazolo[1,5-α]quinazoline

Prepared from 1-acetylpiperazine as described for Example 1, step c (0.068 g, 73%). Found: C, 64.61; H, 4.91; N, 21.53. $C_{21}H_{19}FN_6 \cdot 0.1(H_2O)$ requires C, 64.31; H, 4.93; N, 21.43%. $\delta_H$ (360 MHz; DMSO) 2.07 (3H, s), 3.61–3.67 (4H, m), 3.71–3.74 (4H, m), 7.35–7.40 (2H, m), 7.42–7.50 (1H, m), 7.79 (1H, dd, J=7 and 7), 8.06–8.13 (2H, m), 8.24 (1H, d, J=7), 8.60 (1H, d, J=7); m/z (ES+) 391 (M+H⁺).

EXAMPLE 13

3-(2-Fluorophenyl)-5-[2-oxopiperazin-4(1H)-yl]-[1,2,3]triazolo[1,5-α]quinazoline Prepared from piperazin-2(1H)-one as described for Example 1, step c (0.031 g, 36%). Found: C, 62.09; H, 4.01; N, 22.53. $C_{19}H_{15}FN_6O \cdot 0.33(H_2O)$ requires C, 61.96; H, 4.29; N, 22.82%. $\delta_H$ (360 MHz; DMSO) 3.45–3.55 (2H, m), 3.85–3.90 (2H, m), 4.19 (2H, s), 7.35–7.40 (2H, m), 7.44–7.46 (1H, m), 7.78 (1H, dd, J=7 and 7), 8.06–8.14 (3H, m), 8.24 (1H, d, J=7), 8.61 (1H, d, J=8); m/z (ES+) 363 (M+H⁺).

EXAMPLE 14

3-(2-Fluorophenyl)-5-(1-methyl-2-oxopiperazin-4-yl)-[1,2,3]triazolo[1,5-α]quinazoline Prepared from 1-methylpiperazin-2(1H)-one as described for Example 1, step c (0.033 g, 73%). $\delta_H$ (360 MHz; DMSO)

2.91 (3H, s), 3.61 (2H, dd, J=6 and 6), 3.96 (2H, dd, J=6 and 6), 4.24 (2H, s), 7.35–7.40 (2H, m), 7.44–7.46 (1H, m), 7.78 (1H, dd, J=7 and 7), 8.06–8.12 (2H, m), 8.23 (1H, d, J=7), 8.59 (1H, d, J=7); m/z (ES+) 377 (M+H$^+$).

EXAMPLE 15

5-[5,6-Dihydroimidazo[1,2-α]pyrazin-7(8H)-y]-7-fluoro-3-(2-fluorophenyl)-[1,2,3]triazolo[1,5-α]quinazoline (a) 7-Fluoro-3-(2-fluorophenyl)-[1,2,3]triazolo[1,5-α]quinazolin-5(4H)-one Prepared from 2-azido-5-fluorobenzoic acid as described for Example 1, step a (1.57 g, 100%). δ$_H$ (360 MHz; DMSO) 7.32–7.37 (2H, m), 7.44–7.50 (1H, m), 7.83–7.89 (2H, m), 7.93 (1H, dd, J=9 and 3), 8.42 (1H, dd, J=9 and 5), 12.60 (1H, br s); m/z (ES+) 299 (M+H$_2$O+H$^+$).

(b) 7-Fluoro-3-(2-fluorophenyl)-5-(4-methylbenzenesulfonyloxy)-[1,2,3]triazolo[1,5-α]quinazoline Prepared from 7-fluoro-3-(2-fluorophenyl)-[1,2,3]triazolo[1,5-α]quinazolin-5(4H)-one as described for Example 1, step b (0.259 g, 80%). δ$_H$ (360 MHz; CDCl$_3$) 2.42 (3H, s), 7.22–7.35 (4H, m), 7.46–7.50 (1H, m), 7.76–7.81 (1H, m), 7.87 (1H, dd, J=7 and 7), 7.94 (1H, dd, J=8 and 2), 8.06 (2H, d, J=7), 8.71 (1H, dd, J=8 and 5); m/z (ES+) 453 (M+H$^+$).

(c) 5-[5,6-Dihydroimidazo[1,2-α]pyrazin-7(8H)-yl-7-fluoro-3-(2-fluorophenyl)-[1,2,3]triazolo[1,5-α]quinazoline Prepared from 5,6,7,8-tetrahydroimidazo[1,2-α]pyrazine and 7-fluoro-3-(2-fluorophenyl)-5-(4-methylbenzenesulfonyloxy)-[1,2,3]triazolo[1,5-α]quinazoline as described for Example 1, step c (0.031 g, 26%). Found: C, 61.72; H, 3.79; N, 23.14. C$_{21}$H$_{15}$F$_2$N$_7$.0.33(H$_2$O) requires C, 61.65; H, 3.86; N, 23.96%. δ$_H$ (360 MHz; CDCl$_3$) 4.09 (2H, dd, J=5 and 5), 4.05 (2H, dd, J=5 and 5), 4.97 (2H, s), 6.93 (1H, d, J=1), 7.07 (1H, d, J=1), 7.21–7.32 (2H, m), 7.37–7.40 (1H, m), 7.67–7.74 (2H, m), 8.06 (1H, ddd, J=7, 7 and 2), 8.75 (1H, dd, J=8 and 5); m/z (ES+) 404 (M+H$^+$).

EXAMPLE 16

5-[Bis(2-methoxyethyl)amino]-3-(2-fluorophenyl)-[1,2,3]triazolo[1,5-α]quinazoline Prepared from bis(2-methoxyethyl)amine as described for Example 1, step c (0.015 g, 17%). δ$_H$ (360 MHz; CDCl$_3$) 3.39 (6H, s), 3.77 (4H, t, J=6), 3.89 (4H, t, J=6), 7.18–7.28 (2H, m), 7.30–7.40 (1H, m), 7.60 (1H, dd J=8 and 8), 7.87 (1H, dd, J=8 and 8), 8.11 (1H, ddd, J=8, 8 and 2), 8.43 (1H, dd, J=8 and 1), 8.67 (1H, d, J=8); m/z (ES+) 396 (M+H$^+$).

EXAMPLE 17

3-(2-Fluorophenyl)-5-(thiomorpholin-4-yl)-[1,2,3]triazolo[1,5-α]quinazoline

Prepared from thiomorpholine as described for Example 1, step c (0.060 g, 71%). Found: C, 61.82; H, 4.55; N, 18.48. C$_{19}$H$_{16}$N$_5$SF.0.33(H$_2$O) requires C, 61.44; H, 4.52; N, 18.85%. δ$_H$ (360 MHz; DMSO) 2.90–2.93 (4H, m), 3.85–3.88 (4H, m), 7.35–7.40 (2H, m), 7.43–7.47 (1H, m), 7.77 (1H, dd, J=8 and 8), 8.04–8.12 (2H, m), 8.15 (1H, d, J=8), 8.58 (1H, d, J=8); m/z (ES+) 366 (M+H$^+$).

EXAMPLE 18

5-[4-(Dimethylamino)piperidin-1-yl]-3-(2-fluorophenyl)-[1,2,3]triazolo[1,5-α]quinazolin Prepared from 4-(dimethylamino)piperidine as described for Example 1, step c (0.059 g, 66%). δ$_H$ (360 MHz; DMSO) 1.65–1.80 (2H, m), 1.90–2.00 (2H, m), 2.25 (6H, s), 2.40–2.50 (1H, m), 3.11 (2H, broad dd, J=12 and 12), 4.14 (2H, broad d, J=13), 7.34–7.39 (2H, m), 7.40–7.48 (1H, m), 7.77 (1H, dd, J=7 and 7), 8.03–8.17 (3H, m), 8.56 (1H, d, J=8); m/z (ES+) 391 (M+H$^+$).

EXAMPLE 19

3-(2-Fluorophenyl)-5-[4-(pyrrolidin-1-yl)piperidin-1-yl]-[1,2,3]triazolo[1,5-α]quinazoline Prepared from 4-(pyrrolidin-1-yl)piperidine as described for Example 1, step c (0.062 g, 65%). δ$_H$ (360 MHz; DMSO) 1.60–1.70 (6H, m), 1.98–2.08 (2H, m), 2.25–2.35 (1H, m), 3.20 (2H, broad dd, J=12 and 12), 4.05 (2H, broad d, J=13), 7.33–7.39 (2H, m), 7.40–7.48 (1H, m), 7.76 (1H, dd, J=8 and 8), 8.05 (1H, dd, J=7 and 7), 8.10–8.16 (2H, m), 8.56 (1H, d, J=8); m/z (ES+) 417 (M+H$^+$).

EXAMPLE 20

3-(2-Fluorophenyl)-5-[4-(piperidin-1-yl)piperidin-1-yl]-[1,2,3]triazolo[1,5-α]quinazoline Prepared from 4-(piperidin-1-yl)piperidine as described for Example 1, step c (0.084 g, 85%). Found: C, 67.42; H, 6.23; N, 18.38. C$_{25}$H$_{27}$N$_6$F.0.9(H$_2$O) requires C, 67.22; H, 6.50; N, 18.81%. δ$_H$ (360 MHz; DMSO) 1.35–1.55 (6H, m), 1.70–1.82 (2H, m), 1.85–1.95 (2H, m), 2.45–2.60 (5H, m, partly obscured by DMSO peak), 3.08 (2H, broad dd, J=12 and 12), 4.15 (2H, broad d, J=13), 7.34–7.39 (2H, m), 7.41–7.46 (1H, m), 7.76 (1H, dd, J=8 and 8), 8.02–8.17 (3H, m), 8.56 (1H, d, J=8); m/z (ES+) 431 (M+H$^+$).

EXAMPLE 21

5-[Bis(2-hydroxyethyl)amino]-3-(2-fluorophenyl)-[1,2,3]triazolo[1,5-α]quinazoline Prepared from bis(2-hydroxyethyl)amine as described for Example 1, step c (0.053 g, 30%). δ$_H$ (400 MHz; DMSO) 3.78–3.82 (8H, m), 4.85 (2H, t, J=5), 7.32–7.37 (2H, m), 7.40–7.45 (1H, m), 7.74 (1H, ddd, J=7, 7 and 1), 8.02 (1H, dd, J=7 and 7), 8.10 (1H, ddd, J=7 and 7), 8.43 (1H, dd, J=8 and 1), 8.56 (1H, d, J=7); m/z (ES+) 368 (1+H$^+$).

EXAMPLE 22

3-(2-Fluorophenyl)-5-(4-oxopiperidin-1-yl)-[1,2,3triazolo[1,5-α]quinazoline

A solution of 3-(2-fluorophenyl)-5-(4-methylbenzenesulfonyloxy)-[1,2,3]triazolo[1,5-α]quinazoline (Example 1, step b) (3.0 g, 6.91 mmol), 4-piperidone monohydrate, hydrochloride salt (1.28 g, 8.3 mmol) and triethylamine (3.0 ml, 21 mmol) in dry N,N-dimethylformamide (25 ml) was stirred at 60° C. under nitrogen for 4 h. The mixture was diluted with water (100 ml) and extracted with 10% methanol:dichloromethane (150 ml). The extract was dried (Na$_2$SO$_4$), filtered and concentrated. The residual solid was washed with diethyl ether-ethyl acetate and dried in vacuo to give 3-(2-fluorophenyl)-5-(4-oxopiperidin-1-yl)-[1,2,3]triazolo[1,5-α]quinazoline (1.90 g, 76%). δ$_H$ (360 MHz; DMSO) 2.67 (4H, t, J=6), 3.99 (4H, t, J=6), 7.33–7.48 (3H, m), 7.78 (1H, dd, J=7 and 7), 8.05–8.11 (2H, m), 8.25 (1H, d, J=8), 8.58 (1H, d, J=8); m/z (ES+) 362 (M+H$^+$).

EXAMPLE 23

5-(1-Ethyl-2-oxopiperazin-4-yl)-3-(2-fluorophenyl)-[1,2,3triazolo]1,5-α]quinazoline Sodium hydride (55% w/w in oil; 0.02 g, 0.46 mmol) was added to a stirred solution of 3-(2-fluorophenyl)-5-(2- oxopiperazin-4(1H)-yl)-[1,2,3]triazolo[1,5-α]quinazoline (0.1 g, 0.28 mmol) (Example 13) and iodoethane (0.15 ml) in N,N-dimethylformamide. The mixture was stirred at 50° C. for 3 h, then cooled and diluted with water (8 ml) and 10% methanol:dichloromethane (10 ml). The two phases were separated by filtration through a teflon membrane and the organic layer was concentrated. Preparative thin layer chromatography on silica, eluting with 5% methanol-dichloromethane, gave 5-(1-ethyl-2-oxopiperazin-4-yl)-3-(2-fluorophenyl)-[1,2,3]triazolo[1,5-α]quinazoline (0.035 g, 32%). $\delta_H$ (360 MHz; CDCl$_3$) 1.20 (3H, t, J=7), 3.52 (2H, q, J=7), 3.67 (2H, dd, J=6 and 6), 3.96 (2H, dd, J=6 and 6), 4.38 (2H, s), 7.20–7.32 (2H, m), 7.35–7.42 (1H, m), 7.65 (1H, dd, J=7 and 7), 7.94 (1H, dd, J=7 and 7), 8.02 (1H, d, J=7), 8.23 (1H, dd, J=7 and 7), 8.72 (1H, d, J=7); m/z (ES+) 391 (M+H$^+$).

EXAMPLE 24

3-(2-Fluorophenyl)-5-(2-oxo-1-propylpiperazin-4-yl)-[1,2,3]triazolo[1,5-α]quinazoline Prepared from iodopropane as for Example 23 to give the title compound (0.046 g, 41%). $\delta_H$ (360 MHz; CDCl$_3$) 0.93 (3H, t, J=7), 1.61 (2H, tq, J=7 and 7), 3.43 (2H, t, J=7), 3.66 (2H, dd, J=6 and 6), 3.96 (2H, dd, J=6 and 6), 4.38 (2H, s), 7.20–7.30 (2H, m), 7.35–7.39 (1H, m), 7.65 (1H, dd, J=7 and 7), 7.94 (1H, dd, J=7 and 7), 8.02 (1H, d, J=7), 8.23 (1H, dd, J=7 and 7), 8.72 (1H, d, J=7); m/z (ES+) 405 (M+H$^+$).

EXAMPLE 25

3-(2-Fluorophenyl)-5-[2-oxo-1-(2-propenyl)piperazin-4-yl]-[1,2,3]triazolo-[1,5-α]quinazoline Prepared from 1-bromoprop-2-ene as for Example 23 to give the title compound (0.027 g, 24%). $\delta_H$ (360 MHz; CDCl$_3$) 3.63 (2H, dd, J=6 and 6), 3.95 (2H, dd, J=6 and 6), 4.10 (2H, d, J=5), 4.40 (2H, s), 5.21–5.26 (2H, m), 5.75–5.85 (1H, m), 7.20–7.30 (2H, m), 7.35–7.39 (1H, m), 7.65 (1H, dd, J=7 and 7), 7.94 (1H, dd, J=7 and 7), 8.02 (1H, d, J=7), 8.10 (1H, dd, J=7 and 7), 8.72 (1H, d, J=7); m/z (ES+) 403 (M+H$^+$).

EXAMPLE 26

3-(2-Fluorophenyl)-5-(4-hydroxy-4-methylpiperidin-1-yl)-[1,2,3]triazolo-[1,5-α]quinazoline Methylmagnesium bromide (3M in diethyl ether, 0.24 ml, 0.72 mmol) was added to a stirred solution of 3-(2-fluorophenyl)-5-(4-oxopiperidin-1-yl)-[1,2,3]triazolo[1,5-α]quinazoline (Example 22) (0.107 g, 0.3 mmol) in dry tetrahydrofuran (2 ml) at room temperature under nitrogen. After stirring for 2 h, the mixture was diluted with water (20 ml) and 1M aqueous citric acid (5 ml). The mixture was extracted with dichloromethane (20 ml) and the organic extract was dried (Na$_2$SO$_4$), filtered and concentrated. Preparative thin layer chromatography on silica, eluting with 2% methanol:dichloromethane, gave 3-(2-fluorophenyl)-5-(4-hydroxy-4-methylpiperidin-1-yl)-[1,2,3]triazolo[1,5-α] quinazoline (0.053 g, 47%). $\delta_H$ (360 MHz; CDCl$_3$) 1.38 (3H, s), 1.75–1.85 (2H, m), 1.90–2.00 (2H, m), 3.56–3.64 (2H, m), 3.83–3.89 (2H, m), 7.20–7.30 (2H, m), 7.30–7.40 (1H, m), 7.60 (1H, dd, J=7 and 7), 7.88 (1H, dd, J=7 and 7), 8.02 (1H, d, J=7), 8.15 (1H, dd, J=7 and 7), 8.68 (1H, d, J=7); m/z (ES+) 378 (M+H$^+$).

EXAMPLE 27

1-{4-[3-(2-Fluorophenyl)-[1,2,3triazolo[1,5-α]quinazolin-5-yl]piperazin-1-yl}propan-1-one $\delta_H$ (400 MHz; CDCl$_3$) 1.20 (3H, t, J=7.4), 2.43 (2H, q, J=7.4), 3.62–3.69 (4H, br m), 3.73–3.79 (2H, br m), 3.88–3.93 (2H, br m), 7.20–7.30 (2H, m), 7.35–7.41 (1H, m), 7.63–7.67 (1H, m), 7.91–7.95 (1H, m), 8.03–8.12 (2H, m), 8.71–8.73 (1H, m); m/z (ES+) 405 (M+H$^+$).

EXAMPLE 28

2,2-Dimethyl-1-{4-[3-(2-fluorophenyl)-[1,2,3]triazolo[1,5-α]quinazolin-5-yl]piperazin-1-yl}propan-1-one $\delta_H$ (400 MHz; DMSO) 1.24 (9H, s), 3.61–3.67 (4H, br m), 3.80–3.87 (4H, br m), 7.35–7.39 (2H, m), 7.42–7.48 (1H, m), 7.76–7.80 (1H, m), 8.06–8.11 (2H, m), 8.24–8.25 (1H, m), 8.58–8.60 (1H, m); m/z (ES+) 433 (M+H$^+$).

EXAMPLE 29

N-[3-(2-Fluorophenyl)-[1,2,3]triazolo[1,5-α]quinazolin-5-yl]-N-methyl-N-(1-methylpiperidin-4-yl)amine Prepared from N-methyl-N-(1-methylpiperidin-4-yl)amine as described for Example 1, step c (0.050 g, 56%). $\delta_H$ (400 MHz; CDCl$_3$) 1.96–2.13 (6H, broad m), 2.32 (3H, s), 2.98–3.01 (2H, broad m), 3.20 (3H, s), 4.17–4.20 (1H, broad m), 6.01–6.04 (1H, broad m), 7.19–7.27 (2H, m), 7.30–7.35 (1H, m), 7.59 (1H, ddd, J=7, 7 and 1), 7.87 (1H, ddd, J=7, 7 and 1), 8.04 (1H, d, J=8), 8.19 (1H, ddd, J=8, 8 and 2), 8.69 (1H, d, J=8); m/z (ES+) 391 (M+H$^+$).

EXAMPLE 30

1-[3-(2-Fluorophenyl)-[1,2,3triazolo[1,5-α]quinazolin-5-yl]-[1,4]diazepan-5-one

Prepared from [1,4]diazepan-5-one as described for Example 1, step c (0.065 g, 75%). $\delta_H$ (400 MHz; CDCl$_3$) 2.95–2.99 (2H, m), 3.58–3.62 (2H, m), 3.85–3.88 (4H, m), 6.01–6.04 (1H, broad m), 7.19–7.30 (2H, m), 7.35–7.41 (1H, m), 7.65 (1H, ddd, J=7, 7 and 1), 7.93 (1H, ddd, J=7, 7 and 1), 7.96 (1H, d, J=8), 8.08 (1H, ddd, J=8, 8 and 2), 8.73 (1H, d, J=8); m/z (ES+) 371 (M+H$^+$).

EXAMPLE 31

3-(2-Fluorophenyl)-5-(piperidin-1-yl)-[1,2,3]triazolo[1,5-α]quinazoline

Prepared from piperidine as described for Example 1, step c (0.030 g, 38%). $\delta_H$ (400 MHz; CDCl$_3$) 1.65–1.79 (2H, m), 1.82–1.91 (4H, m), 3.59 (4H, m), 7.19–7.30 (2H, m), 7.31–7.38 (1H, m), 7.60 (1H, ddd, J=7, 7 and 1), 7.86 (1H, ddd, J=7, 7 and 1), 8.01 (1H, dd, J=8 and 1), 8.17 (1H, ddd, J=8, 8 and 2), 8.67 (1H, dd, J=8 and 1); m/z (ES+) 348 (M+H$^+$).

EXAMPLE 32

3-(2-Fluorophenyl)-5-[4-(morpholin-4-yl)piperidin-1-yl]-[1,2,3]triazolo[1,5-α]quinazoline Sodium triacetoxyborohydride (0.53 g, 2.75 mmol) was added portionwise over 10 min to a solution of 3-(2-fluorophenyl)-5-(4-oxopiperidin-1-yl)-[1,2,3]triazolo[1,5-α]quinazoline (0.30 g, 0.83 mmol) and morpholine (0.36 g, 4.1 mmol) in CH$_2$Cl$_2$ (5 ml) and the mixture was allowed to stir for a further 48 h. The mixture was diluted with CH$_2$Cl$_2$ (150 ml), washed with water (50 ml) and brine (50 ml), dried over MgSO$_4$ and evaporated to give a yellow oil. Purification by flash column chromatography on silica eluting with CH$_2$Cl$_2$:MeOH (98:2) followed by trituration with diethyl ether gave 3-(2-fluorophenyl)-5-[4-(morpholin-4-yl)piperidin-1-yl]-[1,2,3]triazolo[1,5-α]quinazoline (0.255 g, 71%) as a white solid. δ$_H$ (400 MHz; CDCl$_3$) 1.78–1.88 (2H, m), 2.04–2.08 (2H, m), 2.43–2.53 (1H, m), 2.58–2.68 (4H, m), 3.07–3.14 (2H, m), 3.75–3.78 (4H, m), 4.17–4.22 (2H, m), 7.19–7.30 (2H, m), 7.33–7.39 (1H, m), 7.61 (1H, ddd, J=8, 8 and 1), 7.88 (1H, ddd, J=8, 8 and 1), 8.00 (1H, d, J=8), 8.13 (1H, ddd, J=7, 7 and 2), 8.69 (1H, d, J=8); m/z (ES+) 433 (M+H$^+$).

EXAMPLE 33

4-(2-Dimethylaminoethyl)-1-[3-(2-fluorophenyl)-[1,2,3]triazolo[1,5-α]quinazolin-5-yl]-[1,4]diazepan-5-one Prepared from 4-(2-dimethylaminoethyl)-[1,4]diazepan-5-one as described for Example 1, step c (0.035 g, 34%). δ$_H$ (360 MHz; CDCl$_3$) 2.25 (6H, s), 2.46 (2H, dd, J=7 and 7), 2.98–3.02 (2H, m), 3.56 (2H, dd, J=7 and 7), 3.73–3.88 (6H, m), 7.19–7.31 (2H, m), 7.35–7.39 (1H, m), 7.64 (1H, ddd, J=7, 7 and 1), 7.92 (1H, ddd, J=7, 7 and 1), 7.96 (1H, dd, J=8 and 1), 8.10 (1H, ddd, J=7, 7 and 2), 8.72 (1H, d, J =8); m/z (ES+) 448 (M+H$^+$).

EXAMPLE 34

1'-[3-(2-Fluorophenyl)-[1,2,3triazolo[1,5-α]quinazolin-5-yl]-[1,4']bipiperidinyl-4-carboxylic acid ethyl ester: oxalate salt Prepared from [1,4']bipiperidinyl-4-carboxylic acid ethyl ester as described for Example 1, step c (0.067 g, 49%). δ$_H$ (400 MHz; DMSO) 1.19 (3H, t, J=7), 1.70–2.15 (8H, m), 2.55–2.68 (1H, m), 2.90–3.07 (2H, m), 3.12–3.19 (2H, m), 3.30–3.40 (3H, m), 4.08 (2H, q, J=7), 4.22–4.26 (2H, m), 7.34–7.40 (2H, m), 7.43–7.49 (1H, m), 7.78 (1H, ddd, J=8, 8 and 1), 8.05–8.11 (2H, m), 8.17 (1H, d, J=8), 8.17 (1H, dd, J=8 and 1); m/z (ES+) 503 (M+H$^+$).

EXAMPLE 35

5-[4-(3,4-Dihydro-1H-isoquinolin-2-yl)piperidin-1-yl]-3-(2-fluorophenyl)-[1,2,3]triazolo[1,5-α]quinazoline Prepared from 2-(piperidin-4-yl)-1,2,3,4-tetrahydroisoquinoline as described for Example 1, step c (0.039 g, 35%). δ$_H$ (400 MHz; CDCl$_3$) 1.92–2.15 (4H, m), 2.76–2.94 (5H, m), 3.11–3.17 (2H, m), 3.87 (2H, s), 4.22–4.27 (2H, m), 7.03–7.30 (6H, m), 7.33–7.39 (1H, m), 7.62 (1H, ddd, J=8, 8 and 1), 7.89 (1H, ddd, J=8, 8 and 1), 8.03 (1H, dd, J=8 and 1), 8.15 (1H, ddd, J=8, 8 and 1), 8.69 (1H, dd, J=8 and 1); m/z (ES+) 479 (M+H$^+$).

EXAMPLE 36

1-{1-[3-(2-Fluorophenyl)-[1,2,3]triazolo[1.5-α]quinazolin-5-yl]piperidin-4-yl}-[1,4]diazepan-5-one Prepared from 1-(piperidin-4-yl)-[1,4]diazepan-5-one as described for Example 1, step c (0.063 g, 60%). δ$_H$ (400 MHz; CDCl$_3$) 1.82–1.95 (4H, m), 2.65–2.68 (2H, m), 2.76–2.85 (5H, m), 3.03–3.11 (2H, m), 3.31–3.35 (2H, m), 4.20–4.24 (2H, m), 5.87–5.91 (1H, broad m), 7.20–7.30 (2H, m), 7.31–7.40 (1H, m), 7.63 (1H, dd, J=7, 7 and 1), 7.90 (1H, ddd, J=7, 7 and 1), 7.96 (1H, dd, J=7 and 1), 8.03 (1H, ddd, J=8, 8 and 2), 8.69 (1H, dd, J=8 and 1); m/z (ES+) 460 (M+H$^+$).

EXAMPLE 37

N,N-Dimethyl-N-{1-[3-(2-fluorophenyl)-[1,2,3]triazolo[1,5-α]quinazolin-5-yl]pyrrolidin-3-yl}amine: oxalate salt Prepared from N,N-dimethyl-N-(pyrrolidin-3-yl)amine as described for Example 1, step c (0.044 g, 41%). δ$_H$ (400 MHz; DMSO) 2.14–2.19 (1H, m), 2.32–2.42 (1H, m), 2.70 (6H, s), 3.60–3.68 (1H, m), 3.98–4.12 (3H, m), 4.21–4.26 (1H, m), 7.31–7.42 (3H, m), 7.74 (1H, ddd, J=8, 8 and 1), 8.05 (1H, ddd, J=8, 8 and 1), 8.17 (1H, ddd, J=7, 7 and 1), 8.48 (1H, d, J =8), 8.58 (1H, dd, J=8 and 1); m/z (ES+) 377 (M+H$^+$).

EXAMPLE 38

3-(2-Fluorophenyl)-5-{4-[2-(pyrrolidin-1-yl)ethyl]piperazin-1-yl}-[1,2,3]triazolo[1,5-α]quinazoline: oxalate salt (a) 4-[3-(2-Fluorophenyl)-[1,2,3]triazolo[1,5-α]quinazolin-5-yl]piperazine-1-carboxylic acid tert-butyl ester A solution of 3-(2-fluorophenyl)-5-(4-methylbenzenesulfonyloxy)-[1,2,3]triazolo[1,5-α]quinazoline (0.33 g, 0.71 mmol), triethylamine (0.3 ml, 2.1 mmol) and piperazine-1-carboxylic acid tert-butyl ester (0.26 g, 1.4 mmol) in dry N,N-dimethylformamide (6 ml) was stirred at 50° C. under nitrogen for 18 h. The mixture was cooled, then diluted with water (30 ml) and extracted with EtOAc (2×75 ml). The combined organic extracts were washed with brine, dried over MgSO$_4$ and evaporated to give a brown oil. Purification by flash column chromatography eluting with CH$_2$Cl$_2$:MeOH (93:7) gave 4-[3-(2-fluorophenyl)-[1,2,3]triazolo[1,5-α]quinazolin-5-yl]piperazine-1-carboxylic acid tert-butyl ester as a white solid (0.28 g, 88%). δ$_H$ (400 MHz; CDCl$_3$) 1.50 (9H, s), 3.59–3.62 (4H, m), 3.69–3.72 (4H, m), 7.19–7.30 (2H, m), 7.32–7.37 (1H, m), 7.63 (1H, ddd, J=8, 8 and 1), 7.91 (1H, ddd, J=8, 8 and 1), 8.02 (1H, d, J=8), 8.11 (1H, ddd, J=7, 7 and 2), 8.70 (1H, dd, J=8 and 1).

(b) 3-(2-Fluorophenyl)-5-(piperazin-1-yl)-[1,2,3triazolo[1,5-α]quinazoline: hydrochloride salt 4-[3-(2-Fluorophenyl)-[1,2,3]triazolo[1,5-α]quinazolin-5-yl]piperazine-1-carboxylic acid tert-butyl ester (0.28 g, 0.63 mmol) was dissolved in dichloromethane (5 ml) and hydrogen chloride bubbled through the reaction (2×10 min). The precipitate was filtered and washed with diethyl ether to give 3-(2-fluorophenyl)-5-(piperazin-1-yl)-[1,2,3]triazolo[1,5-α]quinazoline as a white solid (0.24 g, 100%). HCl salt: δ$_H$ (360 MHz; DMSO) 3.30–3.41 (4H, m), 3.79–3.83 (4H, m), 7.35–7.41 (2H, m), 7.44–7.51 (1H, m), 7.78 (1H, ddd, J=8, 8 and 1), 8.05–8.12 (2H, m), 8.27 (1H, d, J=8), 8.62 (1H, dd, J=8 and 1); m/z (ES+) 349 (M+H$^+$).

(c) 3-(2-Fluorophenyl)-5-{4-[2-(pyrrolidin-1-yl)ethyl]piperazin-1-yl)-[1,2,3]triazolo[1,5-α]quinazoline 3-(2-Fluorophenyl)-5-(piperazin-1-yl)-[1,2,3]triazolo[1,5-α]quinazoline (0.10 g, 0.26 mmol), 1-(2-chloroethyl)pyrrolidine hydrochloride (0.088 g, 0.52 mmol) and triethylamine (0.18 ml, 1.3 mmol) were dissolved in N,N-dimethylformamide (4 ml) and stirred at 80° C. under nitrogen for 18 h. The mixture was cooled, then diluted with water (20 ml) and extracted with CH$_2$Cl$_2$ (2×50 ml). The combined organics were washed with brine (20 ml), dried over MgSO$_4$ and evaporated to give a brown oil. Purification by preparative thin layer chromatography eluting with CH$_2$Cl$_2$:MeOH:NH$_3$(c) (92:8:0.8) gave 3-(2-fluorophenyl)-5-{4-[2-(pyrrolidin-1-yl)ethyl]piperazin-1-yl}-[1,2,3]triazolo[1,5-α]quinazoline as a white solid (0.055 g, 47%).

Oxalate salt (EtOH): $\delta_H$ (400 MHz; DMSO) 1.87–1.98 (4H, m), 2.49–2.52 (6H, m, partly obscured by DMSO peak), 2.66–2.78 (6H, m), 3.30–3.35 (2H, m, partly obscured by H2O peak), 3.60–3.72 (2H, m), 7.33–7.39 (2H, m), 7.43–7.49 (1H, m), 7.77 (1H, ddd, J=8, 8 and 1), 8.05–8.13 (2H, m), 8.19 (1H, d, J=8), 8.59 (1H, dd, J=8 and 1); m/z (ES+) 446 (M+H$^+$).

EXAMPLE 39

3-(2-Fluorophenyl)-5-(4-methoxypiperidin-1-yl)-[1,2,3]triazolo[1,5-α]quinazoline Sodium hydride (60% dispersion in oil) (0.044 g, 1.10 mmol) was added to a solution of 3-(2-fluorophenyl)-5-(4-hydroxypiperidin-1-yl)-[1,2,3]triazolo[1,5-α]quinazoline (Example 9) (10 g, 0.27 mmol) in N,N-dimethylacetamide (4 ml). The mixture was stirred for 30 min before addition of methyl iodide (0.17 ml, 2.8 mmol) and then stirred for a further 18 h. The mixture was diluted with water (20 ml) and extracted with CH$_2$Cl$_2$ (2×50 ml). The combined organic extracts were washed with brine (20 ml), dried over MgSO$_4$ and evaporated to give a colourless oil. Purification by preparative thin layer chromatography eluting with CH$_2$Cl$_2$:MeOH:NH$_3$(c) (95:5:0.5) gave 3-(2-fluorophenyl)-5-(4-methoxypiperidin-1-yl)-[1,2,3]triazolo[1,5-α] quinazoline (0.067 g, 65%) as a yellow solid. $\delta_H$ (360 MHz; CDCl$_3$) 1.84–1.90 (2H, m), 2.11–2.16 (2H, m), 3.36–3.41 (2H, m), 3.42 (3H, s), 3.51–3.54 (1H, m), 3.88–3.95 (2H, m), 7.19–7.29 (2H, m), 7.32–7.37 (1H, m), 7.60 (1H, ddd, J=8, 8 and 1), 7.88 (1H, ddd, J=8, 8 and 1), 8.01 (1H, d, J=8), 8.15 (1H, ddd, J=7, 7 and 2), 8.67 (1H, dd, J=8 and 1); m/z (ES+) 378 (M+H$^+$).

EXAMPLE 40

1-Cyclopropylmethyl-4-[3-(2-fluorophenyl)-[2,3] triazolo[1,5-a ]quinazolin-5-yl]piperazin-2-one Sodium hydride (60% dispersion in oil) (0.40 g, 10.0 mmol) was added portionwise over 10 min to a solution of 3-oxopiperazine-1-carboxylic acid tert-butyl ester (1.00 g, 5.0 mmol) in N,N-dimethylacetamide (10 ml). The mixture was stirred for 30 min before addition of bromomethylcyclopropane (1.45 ml, 15.0 mmol) and then stirred for a further 18 h. The mixture was diluted with water (100 ml) and extracted with EtOAc (2×100 ml). The combined organic extracts were washed with brine (50 ml), dried over MgSO$_4$ and evaporated to give 4-cyclopropylmethyl-3-oxopiperazine-1-carboxylic acid tert-butyl ester (1.27 g, 100%) as a yellow oil. This oil was dissolved in dichloromethane and hydrogen chloride bubbled through the reaction (2×10 min). The solvent was evaporated to give 1-cyclopropylmethylpiperazin-2-one.HCl (0.95 g, 100%) as a white solid.

A solution of 3-(2-fluorophenyl)-5-(4-methylbenzenesulfonyloxy)-[1,2,3]triazolo[1,5-α] quinazoline (0.10 g, 0.23 mmol), triethylamine (1 ml, 7.2 mmol) and 1-cyclopropylmethylpiperazin-2-one.HCl (0.22 g, 1.15 mmol) in dry N,N-dimethylformamide (2 ml) was stirred at 50° C. under nitrogen for 18 h. The mixture was cooled, then diluted with water (15 ml) and extracted with EtOAc (2×75 ml). The combined organic extracts were washed with brine, dried over MgSO$_4$ and evaporated to give a brown oil. Purification by preparative thin layer chromatography eluting with CH$_2$Cl$_2$:MeOH (93:7) gave 1-cyclopropylmethyl-4-[3-(2-fluorophenyl)-[1,2,3]triazolo[1,5-α]quinazolin-5-yl]piperazin-2-one (0.020 g, 21%) as a white solid. $\delta_H$ (400 MHz; CDCl$_3$) 0.26–0.31 (2H, m), 0.52–0.58 (2H, m), 0.99–1.05 (1H, m), 3.37 (2H, d, J=7), 3.77 (2H, dd, J=5 and 5), 3.97 (2H, dd, J=5 and 5), 4.39 (2H, s), 7.20–7.31 (2H, m), 7.35–7.41 (1H, m), 7.66 (1H, dd, J=7 and 7), 7.94 (1H, dd, J=8 and 8), 8.02–8.11 (2H, m), 8.72 (1H, d, J=8); m/z (ES+) 417 (M+H$^+$).

What is claimed is:

1. A compound of formula I, or a pharmaceutically acceptable salt thereof:

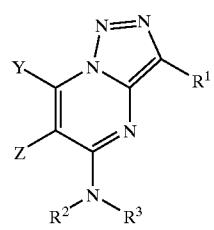

(I)

wherein:

Y represents hydrogen or C$_{1-6}$ alkyl; and

Z represents C$_{1-6}$ alkyl, C$_{3-7}$ cycloalkyl, C$_{4-7}$ cycloalkenyl, C$_{6-8}$ bicycloalkyl, phenyl, naphthyl, azetidinyl, pyrrolidinyl, piperidinyl, piperazinyl, morpholinyl, thiomorpholinyl, diazepanyl, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, C$_{2-7}$ alkoxycarbonyl or di(C$_{1-6}$)alkylamino, which groups are unsubstituted or substituted with one or more substituents selected from: C$_{1-6}$alkyl, phenyl(C$_{1-6}$)alkyl, naphthyl(C$_{1-6}$)alkyl, pyridyl(C$_{1-6}$)alkyl, halogen, halo(C$_{1-6}$)alkyl, cyano, cyano(C$_{1-6}$)alkyl, hydroxy, hydroxymethyl, C$_{1-6}$alkoxy, C$_{3-7}$ cycloalkyl(C$_{1-6}$)alkoxy, C$_{3-7}$ cycloalkoxy, amino(C$_{1-6}$)alkyl, di(C$_{1-6}$alkylamino (C$_{1-6}$alkyl, di(C$_{1-6}$)alkylamino-carbonyl(C$_{1-6}$)alkyl, N-(C$_{1-6}$)alkylpiperidinyl, pyrrolidinyl(C$_{1-6}$alkyl, piperazinyl(C$_{1-6}$)alkyl, morpholinyl(C$_{1-6}$)alkyl, di(C$_{1-6}$)alkylmorpholinyl(C$_{1-6}$)alkyl and imidazolyl (C$_{1-6}$)alkyl; or Y and Z are taken together with the two intervening carbon atoms to form a ring selected from C$_{5-9}$ cycloalkenyl, C$_{6-10}$ bicycloalkenyl, tetrahydropyridinyl, pyridinyl and phenyl, any of which rings may be benzo-fused, or unsubstituted or substituted with one or more substituents selected from: C$_{1-6}$alkyl, phenyl(C$_{1-6}$alkyl, naphthyl(C$_{1-6}$)alkyl, pyridyl(C$_{1-6}$)alkyl, halogen, halo(C$_{1-6}$)alkyl, cyano, cyano(C$_{1-6}$)alkyl, hydroxy, hydroxymethyl, C$_{1-6}$alkoxy, C$_{3-7}$ cycloalkyl(C$_{1-6}$)alkoxy, C$_{3-7}$ cycloalkoxy, amino(C$_{1-6}$)alkyl, di(C$_{1-6}$)alkylamino (C$_{1-6}$)alkyl, di(C$_{1-6}$)alkylamino-carbonyl(C$_{1-6}$)alkyl, N-(C$_{1-6}$)alkylpiperidinyl, pyrrolidinyl(C$_{1-6}$alkyl, piperazinyl(C$_{1-6}$)alkyl, morpholinyl(C$_{1-6}$)alkyl, di(C$_{1-6}$)alkylmorpholinyl(C$_{1-6}$)alkyl and imidazolyl (C$_{1-6}$)alkyl;

R$^1$ represents C$_{3-7}$ cycloalkyl, phenyl, furyl, thienyl or pyridinyl, which groups may be unsubstituted or substituted with one or more substituents selected from: C$_{1-6}$alkyl, phenyl(C$_{1-6}$)alkyl, naphthyl(C$_{1-6}$)alkyl, pyridyl(C$_{1-6}$)alkyl, halogen, halo(C$_{1-6}$)alkyl, cyano, cyano(C$_{1-6}$)alkyl, hydroxy, hydroxymethyl, $C_{1-6}$alkoxy, $C_{3-7}$ cycloalkyl($C_{1-6}$)alkoxy, $C_{3-7}$ cycloalkoxy, amino($C_{1-6}$)alkyl, di($C_{1-6}$alkylamino ($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl ($C_{1-6}$)alkyl;

$R^2$ represents hydrogen, $C_{1-6}$ alkyl, hydroxy($C_{1-6}$)alkyl or $C_{1-6}$ alkoxy($C_{1-6}$)alkyl; and $R^3$ represents $C_{1-6}$ alkyl, $C_{3-7}$ cycloalkyl($C_{1-6}$)alkyl, phenyl($C_{1-6}$)alkyl, naphthyl($C_{1-6}$)alkyl, azetidinyl, pyrrolidinyl, piperidinyl, piperazinyl, morpholinyl, thiomorpholinyl, diazepanyl, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl or quinoxalinylmethyl, any of which groups are unsubstituted or substituted with one or more substituents selected from: $C_{1-6}$alkyl, phenyl($C_{1-6}$)alkyl, naphthyl ($C_{1-6}$)alkyl, pyridyl($C_{1-6}$)alkyl, halogen, halo($C_{1-6}$) alkyl, cyano, cyano($C_{1-6}$)alkyl, hydroxy, hydroxymethyl, $C_{1-6}$alkoxy, $C_{3-7}$ cycloalkyl($C_{1-6}$) alkoxy, $C_{3-7}$ cycloalkoxy, amino($C_{1-6}$)alkyl, di($C_{1-6}$) alkylamino($C_{1-6}$)alkyl, di($C_{1-6}$)alkylaminocarbonyl ($C_{1-6}$)alkyl, N-($C_{1-6}$)alkylpiperidinyl, pyrrolidinyl ($C_{1-6}$)alkyl, piperazinyl($C_{1-6}$)alkyl, morpholinyl($C_{1-6}$) alkyl, di($C_{1-6}$)alkylmorpholinyl($C_{1-6}$)alky and imidazolyl($C_{1-6}$)alkyl;

$R^2$ and $R^3$ are taken together with the intervening nitrogen atom to form a ring of formula (a), (b), (c), (d), (e), (f), (g), (h), (j) or (k):

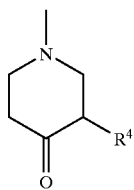 (a)

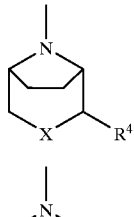 (b)

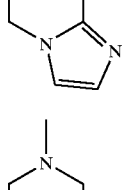 (c)

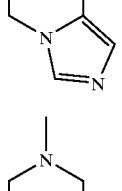 (d)

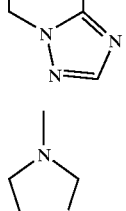 (e)

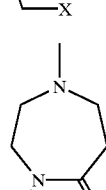 (f)

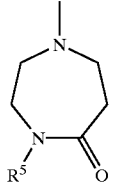 (g)

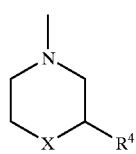 (h)

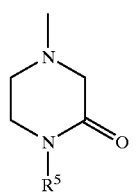 (j)

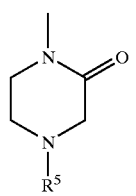 (k)

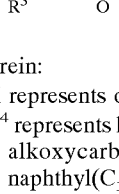

wherein:
X represents oxygen, sulphur, N—$R^5$ or $CR^6R^7$;
$R^4$ represents hydrogen, $C_{1-6}$ alkyl, phenyl, naphthyl, $C_{2-7}$ alkoxycarbonyl, phenyl($C_{1-6}$)alkoxy($C_{1-6}$)alkyl or naphthyl($C_{1-6}$)alkoxy($C_{1-6}$)alkyl;
$R^5$ represents hydrogen, $C_{1-6}$ alkyl, di($C_{1-6}$)alkylamino ($C_{1-6}$)alkyl, $C_{2-6}$ alkenyl, $C_{3-7}$ cycloalkyl($C_{1-6}$)alkyl, phenyl, naphthyl, azetidinyl($C_{1-6}$)alkyl, pyrrolidinyl ($C_{1-6}$)alkyl, piperidinyl($C_{1-6}$)alkyl, piperazinyl($C_{1-6}$) alkyl, morpholinyl($C_{1-6}$)alkyl, thiomorpholiny($C_{1-6}$) alkyl, diazepanyl($C_{1-6}$)alkyl, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, $C_{2-7}$ alkylcarbonyl or $C_{2-7}$ alkoxycarbonyl;

$R^6$ represents hydrogen, halogen, hydroxy, $C_{1-6}$ alkoxy, di($C_{1-6}$)alkylamino, $C_{2-7}$ alkoxycarbonyl, a azetidinyl, pyrrolidinyl, piperidinyl, piperazinyl, morpholinyl, thiomorpholinyl, or diazepanyl group which may be phenyl fused and which is unsubstituted or substituted with one or more substituents selected from: $C_{1-6}$alkyl, phenyl($C_{1-6}$)alkyl, naphthyl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$ cycloalkyl($C_{1-6}$)alkoxy, $C_{3-7}$ cycloalkoxy, amino($C_{1-6}$)alkyl, di($C_{1-6}$alkylamino($C_{1-6}$)alkyl, di($C_{1-6}$)alkylaminocarbonyl($C_{1-6}$)alkyl, N-($C_{1-6}$alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl; and $R^7$ represents hydrogen, $C_{1-6}$ alkyl, or phenyl, naphthyl, phenyl($C_{1-6}$)alkyl or naphthyl($C_{1-6}$)alkyl group which is unsubstituted or substituted with one or more substituents selected from: $C_{1-6}$alkyl, phenyl($C_{1-6}$)alkyl, naphthyl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$ cycloalkyl($C_{1-6}$)alkoxy, $C_{3-7}$ cycloalkoxy, amino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl.

2. The compound of claim 1 of formula IIA, or a pharmaceutically acceptable salt thereof:

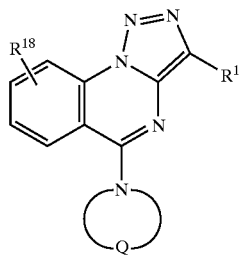

(IIA)

wherein:

$R^{18}$ represents hydrogen or halogen; and

Q represents the residue of a ring of formula (a), (b), (c), (d), (e), (f), (g), (h), (j) or (k) as defined in claim 1.

3. The compound of claim 1 of formula IIB, or a pharmaceutically acceptable salt thereof:

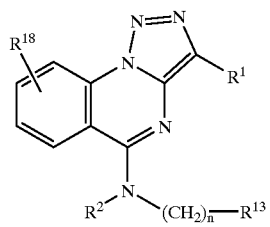

(IIB)

wherein:

$R^{18}$ represents hydrogen or halogen;

n is 1 or 2; and $R^{13}$ represents hydroxy or $C_{1-6}$ alkoxy, or a phenyl, naphthyl, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl or tetrazolyl group, which group is unsubstituted or substituted with one or more substituents selected from: $C_{1-6}$alkyl, phenyl($C_{1-6}$)alkyl, naphthyl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$ cycloalkyl($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$)alkylamino-carbonyl($C_{1-6}$alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl ($C_{1-6}$)alkyl.

4. The compound of claim 3 of formula IIC, or a pharmaceutically acceptable salt thereof:

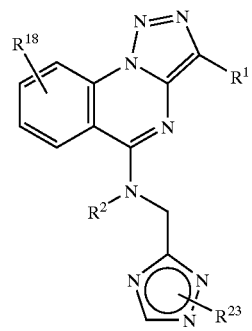

(IIC)

wherein:

$R^{23}$ represents hydrogen, methyl or ethyl.

5. The compound of claim 1 formula IID, or a pharmaceutically acceptable salt thereof:

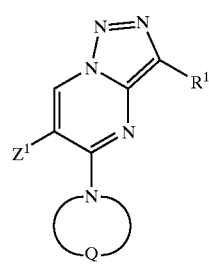

(IID)

wherein:

Q represents the residue of a ring of formula (a), (b), (c), (d), (e), (f), (g), (h), (j) or (k) as defined in claim 1; and $Z^1$ represents $C_{1-6}$ alkyl, $C_{3-7}$ cycloalkyl or phenyl, naphthyl group, which group is unsubstituted or substituted with one or more substituents selected from: $C_{1-6}$alkyl, phenyl($C_{1-6}$)alkyl, naphthyl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$ cycloalkyl($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$ alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl.

6. The compound of claim 1 of the formula IIE, and salts thereof:

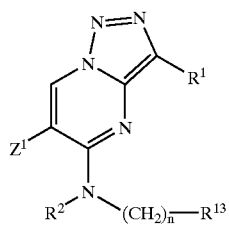

(IIE)

wherein:

n is 1 or 2;

$R^{13}$ represents hydroxy or $C_{1-6}$ alkoxy, or a phenyl, naphthyl, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, or tetrazolyl group, which group is unsubstituted or substituted with one or more substituents selected from: $C_{1-6}$alkyl, phenyl($C_{1-6}$)alkyl, naphthyl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$ cycloalkyl($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl; and $Z^1$ represents $C_{1-6}$ alkyl, $C_{3-7}$ cycloalkyl, phenyl or naphthyl group, which group is unsubstituted or substituted with one or more substituents selected from: $C_{1-6}$alkyl, phenyl($C_{1-6}$)alkyl, naphthyl($C_{1-6}$)alkyl, pyridyl($C_{1-6}$)alkyl, halogen, halo($C_{1-6}$)alkyl, cyano, cyano($C_{1-6}$)alkyl, hydroxy, hydroxymethyl, $C_{1-6}$alkoxy, $C_{3-7}$ cycloalkyl($C_{1-6}$)alkoxy, $C_{3-7}$ cycloalkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$ alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl and imidazolyl($C_{1-6}$)alkyl.

7. The compound of claim 6 represented by formula IIF, and salts thereof:

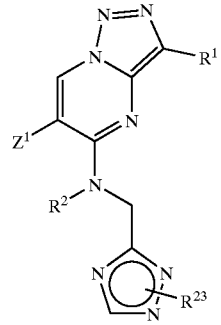

(IIF)

wherein:

$R^{23}$ represents hydrogen, methyl or ethyl.

8. The compound of claim 1 which is selected from the group consisting of:

3-(2-fluorophenyl)-5-(morpholin-4-yl)-[1,2,3]triazolo[1,5-α]quinazoline;

5-[5,6-dihydroimidazo]1,2-α]pyrazin-7(8H)-yl]-3-(2-fluorophenyl)-[1,2,3]triazolo[1,5-α]quinazoline;

5-5,6-dihydroimidazo]1,5-α]pyrazin-7(8H)-yl]-3-(2-fluorophenyl)-[1,2,3]triazolo[1,5-α]quinazoline;

5-[5,6-dihydro[1,2,4]triazolo[1,5-α]pyrazin-7(8H)-yl]-3-(2-fluorophenyl)-[1,2,3]triazolo[1,5-α]quinazoline;

3-(2-fluorophenyl)-5-(3-oxo-4-phenylpiperazin-1-yl)-[1,2,3]triazolo[1,5-α]quinazoline;

5-(4-ethoxycarbonylpiperazin-1-yl)-3-(2-fluorophenyl)-[1,2,3]triazolo[1,5-α]quinazoline;

5-(3-ethoxycarbonylpiperidin-1-yl)-3-(2-fluorophenyl)-[1,2,3]triazolo[1,5-α]quinazoline;

5-(4-ethoxycarbonylpiperidin-1-yl)-3-(2-fluorophenyl)-[1,2,3]triazolo[1,5-α]quinazoline;

3-(2-fluorophenyl)-5-(4-hydroxypiperidin-1-yl)-[1,2,3]triazolo[1,5-α]quinazoline;

3-(2-fluorophenyl)-5-[4-(pyridin-4-yl)piperazin-1-yl]-[1,2,3]triazolo[1,5-α]quinazoline;

3-(2-fluorophenyl)-5-[4-(pyridin-2-yl)piperazin-1-yl]-[1,2,3]triazolo[1,5-α]quinazoline;

5-(4-acetylpiperazin-1-yl)-3-(2-fluorophenyl)-[1,2,3]triazolo[1,5-α]quinazoline;

3-(2-fluorophenyl)-5-[2-oxopiperazin-4(1H)-yl]-[1,2,3]triazolo[1,5-α]quinazoline;

3-(2-fluorophenyl)-5-(1-methyl-2-oxopiperazin-4-yl)-[1,2,3]triazolo[1,5-α]quinazoline;

5-[5,6-dihydroimidazo[1,2-α]pyrazin-7(8H)-yl]-7-fluoro-3-(2-fluorophenyl)-[1,2,3]triazolo[1,5-α]quinazoline;

5-[bis(2-methoxyethyl)amino]-3-(2-fluorophenyl)-[1,2,3]triazolo[1,5-α]quinazoline;

3-(2-fluorophenyl)-5-(thiomorpholin-4-yl)-[1,2,3]triazolo[1,5-α]quinazoline;

5-[4-(dimethylamino)piperidin-1-yl]-3-(2-fluorophenyl)-[1,2,3]triazolo[1,5-α]quinazoline;

3-(2-fluorophenyl)-5-[4-(pyrrolidin-1-yl)piperidin-1-yl]-[1,2,3]triazolo[1,5-α]quinazoline;

3-(2-fluorophenyl)-5-[4-(piperidin-1-yl)piperidin-1-yl]-[1,2,3]triazolo[1,5-α]quinazoline;

5-[bis(2-hydroxyethyl)amino]-3-(2-fluorophenyl)-[1,2,3]triazolo[1,5-α]quinazoline;

3-(2-fluorophenyl)-5-(4-oxopiperidin-1-yl)-[1,2,3]triazolo[1,5-α]quinazoline;

5-(1-ethyl-2-oxopiperazin-4-yl)-3-(2-fluorophenyl)-[1,2,3]triazolo[1,5-α]quinazoline;

3-(2-fluorophenyl)-5-(2-oxo-1-propylpiperazin-4-yl)-[1,2,3]triazolo[1,5-α]quinazoline;

3-(2-fluorophenyl)-5-[2-oxo-1-(2-propenyl)piperazin-4-yl]-[1,2,3]triazolo-[1,5-α]quinazoline;

3-(2-fluorophenyl)-5-(4-hydroxy-4-methylpiperidin-1-yl)-[1,2,3]triazolo-[1,5-α]quinazoline;

1-{4-[3-(2-fluorophenyl)-[1,2,3]triazolo[1,5-α]quinazolin-5-yl]piperazin-1-yl)}propan-1-one;

2,2-dimethyl-1-{4-[3-(2-fluorophenyl)-[1,2,3]triazolo[1,5-α]quinazolin-5-yl]piperazin-1-yl}propan-1-one; and salts thereof.

9. The compound of claim 1 which is selected from the group consisting of:

N-[3-(2-fluorophenyl)-[1,2,3]triazolo[1,5-α]quinazolin-5-yl]-N-methyl-N-(1-methylpiperidin-4-yl)amine;

1-[3-(2-fluorophenyl)-[1,2,3]triazolo[1,5-α]quinazolin-5-yl]-[1,4]diazepan-5-one;

3-(2-fluorophenyl)-5-(piperidin-1-yl)-[1,2,3]triazolo[1,5-α]quinazolin;

3-(2-fluorophenyl)-5-[4-(morpholin-4-yl)piperidin-1-yl]-[1,2,3]triazolo[1,5-α]quinazoline;

4-(2-dimethylaminoethyl)-1-[3-(2-Fluorophenyl)-[1,2,3]triazolo[1,5-α]quinazolin-5-yl]-1,4]diazepan-5-one;

1'-[3-(2-fluorophenyl)-[1,2,3]triazolo[1,5-α]quinazolin-5-yl]-[1,4']bipiperidinyl-4-carboxylic acid ethyl ester;

5-[4-(3,4-dihydro-1H-isoquinolin-2-yl)piperidin-1-yl]-3-(2-fluorophenyl)-[1,2,3]triazolo[1,5-α]quinazoline;

1-{1-[3-(2-fluorophenyl)-[1,2,3]triazolo[1,5-α]quinazolin-5-yl]piperidin-4-yl}-[1,4]diazepan-5-one;

N,N-dimethyl-N-{1-[3-(2-fluorophenyl)-[1,2,3]triazolo[1,5-α]quinazolin-5-yl]pyrrolidin-3-yl}amine;

3-(2-fluorophenyl)-5-{4-[2-(pyrrolidin-1-yl)ethyl]piperazin-1-yl}-[1,2,3]triazolo[1,5-α]quinazoline;

3-(2-fluorophenyl)-5-(4-methoxypiperidin-1-yl)-[1,2,3]triazolo[1,5-α]quinazoline;

1-cyclopropylmethyl-4-[3-(2-fluorophenyl)-[1,2,3]triazolo[1,5-α]quinazolin-5-yl]piperazin-2-one;

and salts thereof.

10. A pharmaceutical composition comprising a compound of claim 1 or a pharmaceutically acceptable salt thereof and a pharmaceutically acceptable carrier.

11. A method for the treatment of anxiety which comprises administering to a patient in need thereof an effective amount of a compound of claim 1 or a pharmaceutically acceptable salt thereof.

12. A method for the prevention of anxiety which comprises administering to a patient in need thereof an effective amount of a compound of claim 1 or a pharmaceutically acceptable salt thereof.

* * * * *